United States Patent
Mizutani et al.

(10) Patent No.: US 9,096,233 B2
(45) Date of Patent: Aug. 4, 2015

(54) VISUAL CONFIRMATION EVALUATING APPARATUS AND METHOD

(71) Applicant: FUJITSU LIMITED, Kawasaki-shi, Kanagawa (JP)

(72) Inventors: Masami Mizutani, Kawasaki (JP); Yasuhiro Aoki, Kawasaki (JP)

(73) Assignee: FUJITSU LIMITED, Kawasaki (JP)

( * ) Notice: Subject to any disclaimer, the term of this patent is extended or adjusted under 35 U.S.C. 154(b) by 0 days.

(21) Appl. No.: 14/184,093

(22) Filed: Feb. 19, 2014

(65) Prior Publication Data

US 2014/0297059 A1    Oct. 2, 2014

(30) Foreign Application Priority Data

Mar. 28, 2013   (JP) .................................. 2013-070344

(51) Int. Cl.
| | |
|---|---|
| G08G 1/00 | (2006.01) |
| G08G 1/04 | (2006.01) |
| G08G 1/16 | (2006.01) |
| B60W 50/00 | (2006.01) |
| A61B 5/18 | (2006.01) |
| G05D 1/02 | (2006.01) |

(52) U.S. Cl.
CPC ................. B60W 50/00 (2013.01); G08G 1/16 (2013.01); A61B 5/18 (2013.01); G05D 1/0246 (2013.01); G05D 1/0251 (2013.01); G08G 1/00 (2013.01); G08G 1/04 (2013.01)

(58) Field of Classification Search
CPC ................................. B60K 35/00; B60K 41/00
USPC .......... 701/1, 36, 45, 117; 340/435, 438, 576, 340/575, 901, 904, 905; 382/154; 348/148
See application file for complete search history.

(56) References Cited

U.S. PATENT DOCUMENTS

| | | | | |
|---|---|---|---|---|
| 8,085,140 | B2 * | 12/2011 | Mochizuki et al. | 340/438 |
| 8,599,027 | B2 * | 12/2013 | Sanchez | 340/576 |
| 8,847,771 | B2 * | 9/2014 | Gunaratne et al. | 340/576 |
| 2009/0303078 | A1 * | 12/2009 | Mochizuki et al. | 340/901 |
| 2010/0054580 | A1 * | 3/2010 | Miyoshi et al. | 382/154 |

FOREIGN PATENT DOCUMENTS

| | | |
|---|---|---|
| EP | 2296124 | 3/2011 |
| JP | 2007-310794 | 11/2007 |
| JP | 2008-181206 | 8/2008 |
| JP | 2009-123182 | 6/2009 |
| WO | 2009-148188 | 12/2009 |

* cited by examiner

*Primary Examiner* — Thomas Tarcza
*Assistant Examiner* — Tyler J Lee
(74) *Attorney, Agent, or Firm* — Fujitsu Patent Center

(57) ABSTRACT

A visual confirmation evaluating apparatus generates unobstructed state information indicating that a driver in a vehicle at an intersection is in a position capable of visually confirming roads on the right and left. This unobstructed state information is used to evaluate a safety check made by the driver, in order to improve the accuracy of the evaluation. In addition, the visual confirmation evaluating apparatus generates viewing direction information indicating a direction in which the driver of the vehicle should look at the intersection, and an appropriateness of a line of sight of the driver is evaluated using the viewing direction information.

19 Claims, 18 Drawing Sheets

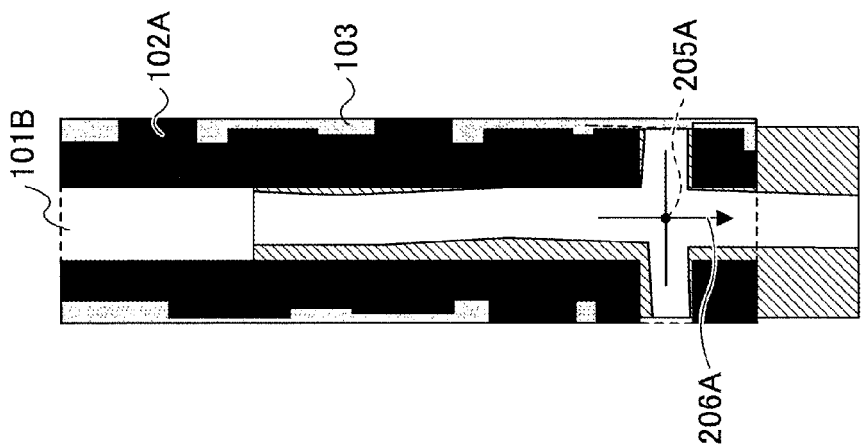
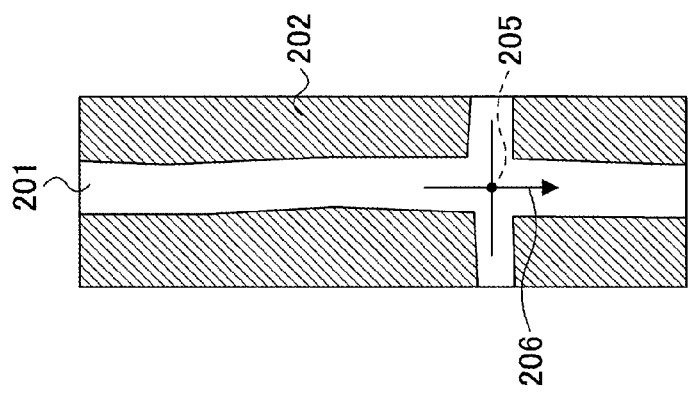
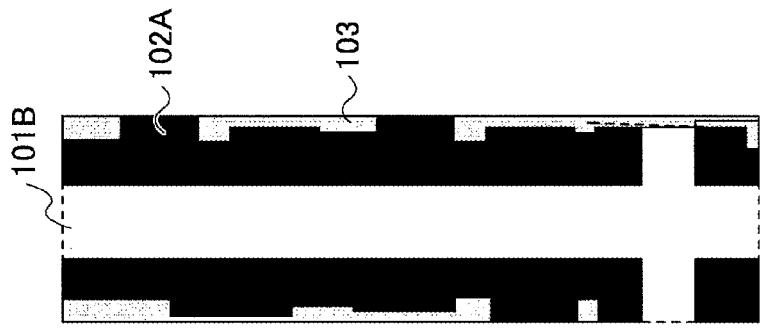

FIG.7A
FIG.7B
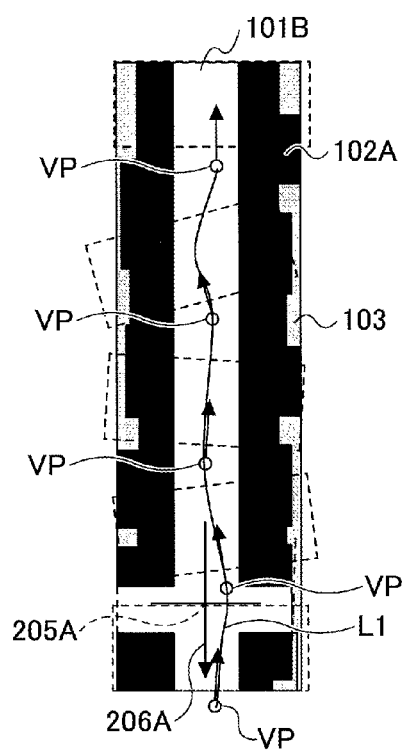
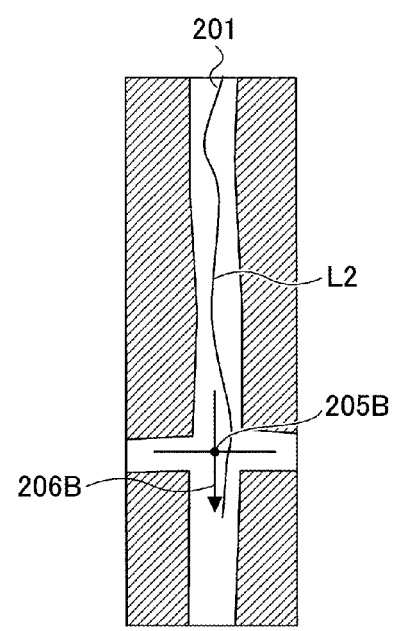

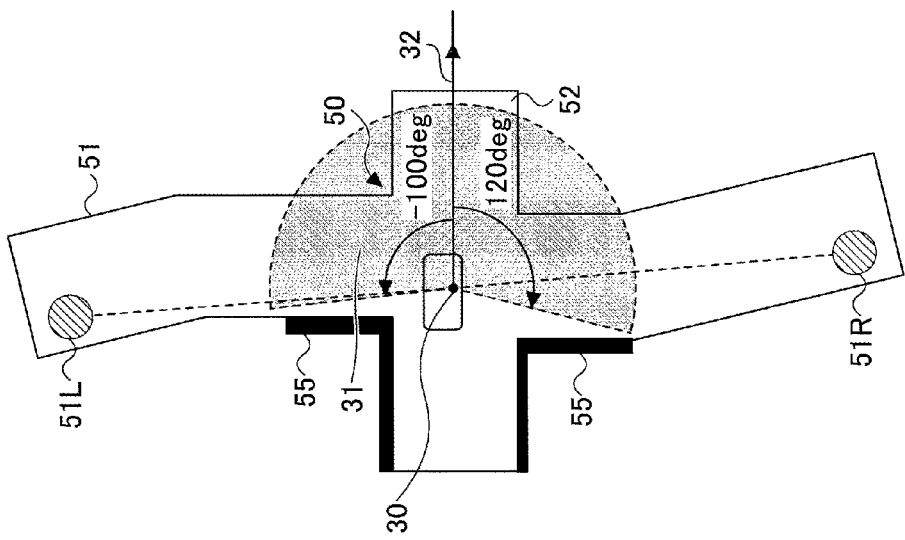
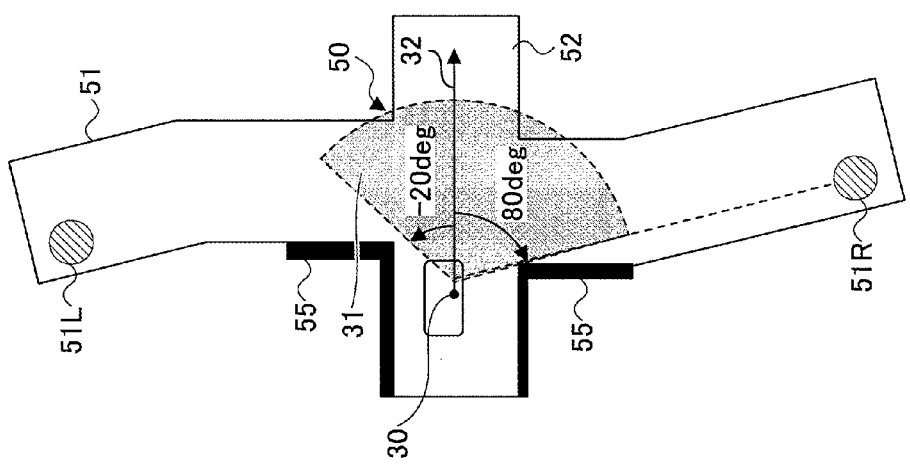
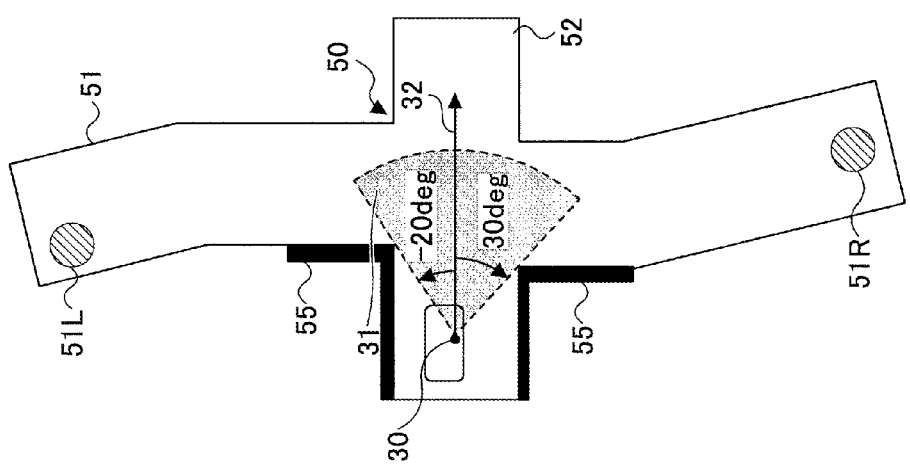

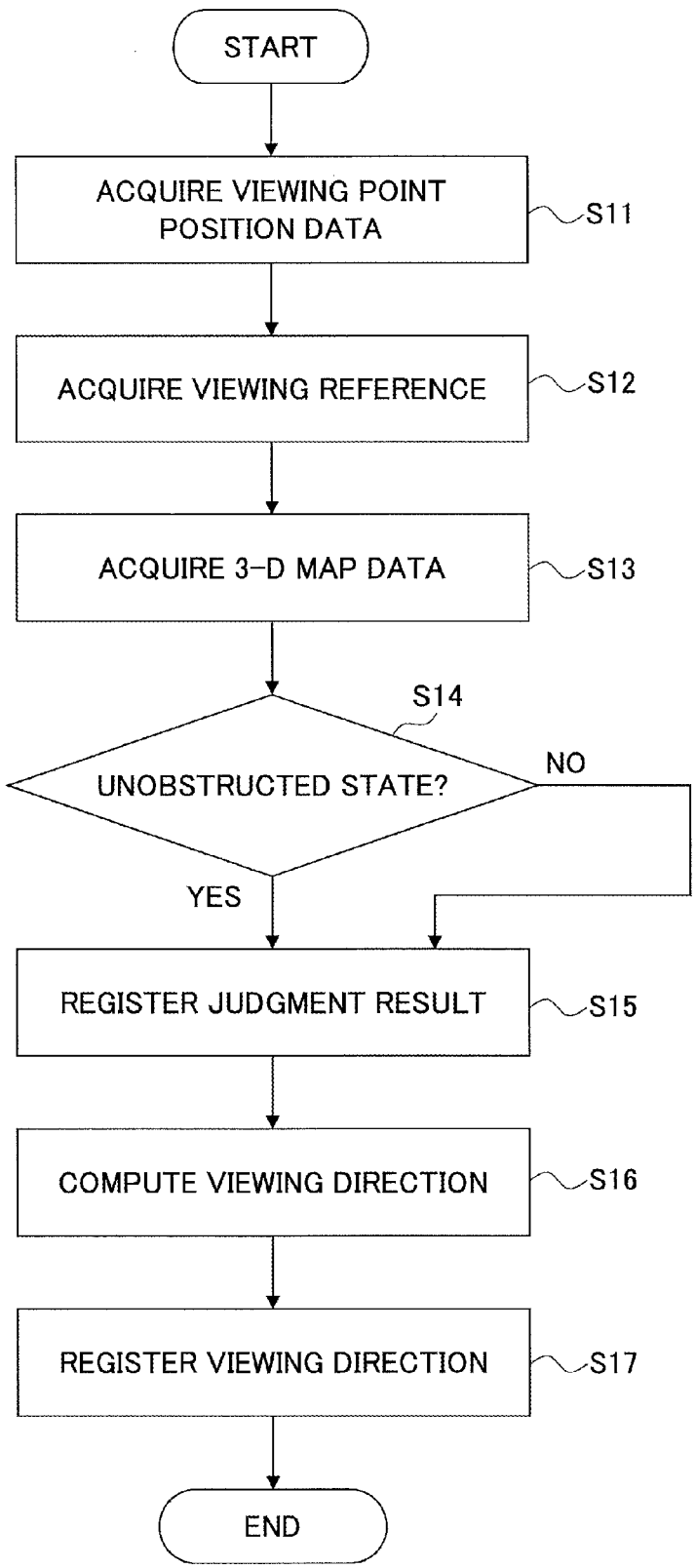

FIG.11

| TIME | $t_i$ | $t_{i+1}$ | $t_{i+2}$ | ... | $t_n$ |
|---|---|---|---|---|---|
| VIEWING DIRECTION | Dir_i | Dir_i+1 | Dir_i+2 | | Dir_n |
| UNOBSTRUCTED STATE | 0 | 1 | 1 | | 0 |
| OTHER ATTRIBUTES | | | | | |

FIG.14

| TIME | $t_i$ | $t_{i+1}$ | $t_{i+2}$ | ... | $t_n$ |
|---|---|---|---|---|---|
| LINE-OF-SIGHT DIRECTION | Gaze_i | Gaze_i+1 | Gaze_i+2 | | Gaze_n |
| VIEWING DIRECTION | Dir_i | Dir_i+1 | Dir_i+2 | | Dir_n |
| UNOBSTRUCTED STATE | 0 | 1 | 1 | | 0 |
| APPROPRIATENESS OF LINE-OF-SIGHT DIRECTION | — | OK | OK | | ... |

| TIME SEGMENT | DURATION TIME | SCORE VALUE SC |
|---|---|---|
| SEGMENT 1 | t_seg1s~tseg1e | SC1_1 |
| SEGMENT 2 | t_seg2s~tseg2e | SC1_2 |
| ... | | |
| SEGMENT k | t_segks~t_final | SC1_3 |

VISUAL CONFIRMATION EVALUATING APPARATUS AND METHOD

CROSS-REFERENCE TO RELATED APPLICATIONS

This application is based upon and claims the benefit of priority of the prior Japanese Patent Application No. 2013-070344, filed on Mar. 28, 2013, the entire contents of which are incorporated herein by reference.

FIELD

The embodiments discussed herein are related to a visual confirmation evaluating apparatus and method, and a computer-readable storage medium.

BACKGROUND

Many of traffic accidents occur at intersections, and many accidents may be prevented by safety checks made by a driver. In techniques related to diagnosing the driver's driving safety, a method has been proposed to evaluate the appropriateness of a safety check operation from the driver's head turn angle at the intersection, based on a movement of the driver's head, a vehicle position, and a vehicle velocity, for example. Such a method is proposed in International Publication No. WO2009/148188, for example.

However, the proposed method described above detects the movement of the driver's head, and it is difficult to know a range that is actually being checked by the driver's eyes. In addition, if the evaluation judges that the safety check is made when the driver's head turn is detected in a predetermined angular range, the driver's actual line of sight may not be facing an appropriate direction. Moreover, the angular range to be checked by the driver differs for each intersection. For these reasons, it is difficult to accurately evaluate the driver's safety check operation.

Further, because the proposed method described above detects the vehicle velocity for use in evaluating the appropriateness of the safety check operation, it is difficult to know whether the driver is at a position having an unobstructed view of the intersection. In other words, the view from the driver within the vehicle may be obstructed by a wall, a building, or the like, for example, and it is impossible to judge from simply the vehicle velocity whether the driver is at a position where the safety check can be made. For this reason, it is difficult to accurately evaluate the driver's safety check operation.

Accordingly, it is difficult to accurately evaluate the appropriateness of the driver's visual confirmation operation.

The applicants are aware of Japanese Laid-Open Patent Publications No. 2007-310794, No. 2008-181206, and No. 2009-123182, for example.

SUMMARY

Accordingly, it is an object in one aspect of the embodiment to provide a visual confirmation evaluating apparatus and method, and a computer-readable storage medium, that can accurately evaluate the appropriateness of the driver's visual confirmation operation.

According to one aspect of the present invention, a visual confirmation evaluating apparatus may include:

a head position acquiring unit configured to acquire head position data indicating a head position of a driver within a vehicle;

a line-of-sight acquiring unit configured to acquire line-of-sight data of the driver;

a velocity acquiring unit configured to acquire velocity data of the vehicle;

a storage unit configured to store three-dimensional map data representing a map of a real world in which the vehicle travels by three-dimensional shape data, and definition data including an identifier to identify each of intersections, a viewing reference, a confirmation time and an elapsed time;

wherein the definition data define the viewing reference in the three-dimensional map data for each of the intersections identified by the identifier, and the viewing reference is position information of a virtual target that is to be confirmed by the driver when the vehicle enters each of the intersections for each road on right and left directions of each of the intersections;

wherein the confirmation time indicates a time required by the driver to make a visual confirmation that is to be made from a position where each of the intersections is visible, wherein the elapsed time indicates a maximum delay time of a timing at which the driver makes a decision to move the vehicle, a position and direction acquiring unit configured to acquire position data and direction data indicating a position and a direction of the vehicle in the three-dimensional map data;

a viewing information generating unit configured to generate viewing direction information indicating a direction towards the viewing reference from the head position of the driver indicated by the head position data, and unobstructed state information indicating a state in which the viewing reference is visible from the driver, based on the head position data, the line-of-sight data, the vehicle position data, the direction data, the definition data and the three-dimensional map data; and a visual confirmation evaluating unit configured to evaluate an appropriateness of a visual confirmation operation of the driver, based on the head position data, the line-of-sight data, the vehicle position data, the direction data, the definition data, the unobstructed state information and the viewing direction information.

The object and advantages of the invention will be realized and attained by means of the elements and combinations particularly pointed out in the claims.

It is to be understood that both the foregoing general description and the following detailed description are exemplary and explanatory and are not restrictive of the invention, as claimed.

BRIEF DESCRIPTION OF DRAWINGS

FIGS. 6A, 6B, and 6C are diagrams for explaining an example of overlapping an intersection template and a difference road orthographic image;

FIGS. 7A and 7B are diagrams for explaining an example of a process to compute a vehicle position and a vehicle direction from virtual position and direction of the rear camera;

FIGS. 9A, 9B, and 9C are diagrams for explaining generation of unobstructed state information and viewing direction information;

FIG. 10 is a flow chart for explaining a viewing direction registration process of a viewing information generating unit;

FIG. 11 is a diagram illustrating an example of results of the viewing direction registration process of the viewing information generating unit;

FIG. 14 is a diagram illustrating an example of results of the line-of-sight direction judging process of the viewing information generating unit;

DESCRIPTION OF EMBODIMENTS

Preferred embodiments of the present invention will be described with reference to the accompanying drawings.

In one embodiment, a visual confirmation evaluating apparatus may generate unobstructed state information indicating that a driver in a vehicle at an intersection is in a position capable of visually confirming roads on the right and left. This unobstructed state information may be used to evaluate a visual confirmation (or safety check) made by the driver, in order to improve the accuracy of the evaluation. In addition, the visual confirmation evaluating apparatus may generate viewing direction information indicating a direction in which the driver of the vehicle should look at the intersection. This viewing direction information may be used to evaluate an appropriateness of a line of sight of the driver. The visual confirmation may be judged to be appropriate when the evaluation based on the unobstructed state information and the evaluation based on the viewing direction information are both good (for example, both have high scores) within a predetermined elapsed time going back in time from a start time at which an acceleration of the vehicle is to start in order to pass the intersection. This start time corresponds to a moving decision-making time or timing at which the driver makes the decision to move the vehicle in order to pass the intersection.

A description will now be given of the visual confirmation evaluating apparatus and method, and the computer-readable storage medium in each embodiment according to the present invention.

First Embodiment

Figure 1:
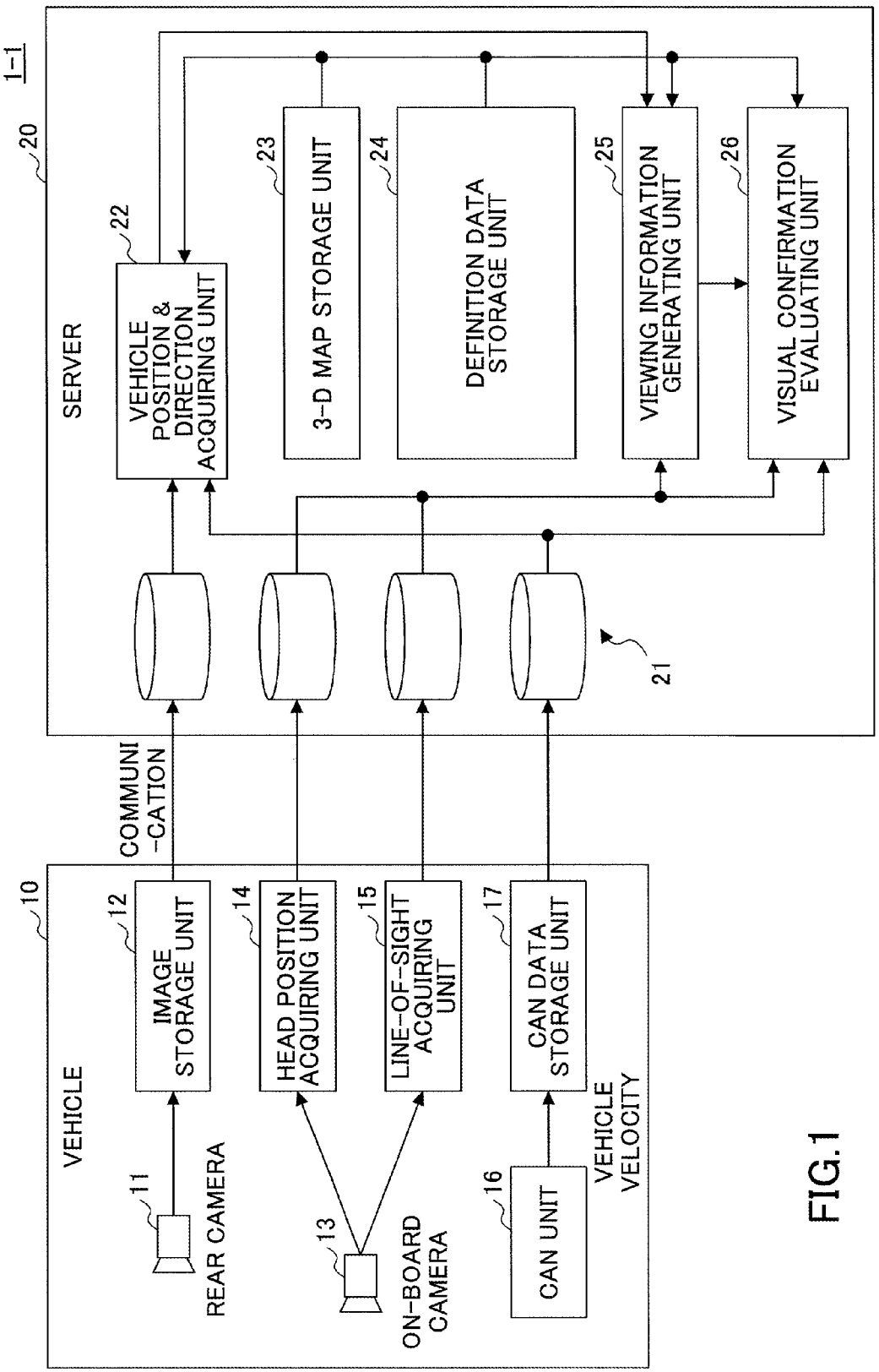
FIG. 1 is a block diagram illustrating an example of a visual confirmation evaluating apparatus in a first embodiment.

First, a description will be given of an example of the visual confirmation evaluating apparatus in a first embodiment, by referring to FIG. 1. FIG. 1 is a block diagram illustrating this example of the visual confirmation evaluating apparatus in the first embodiment. A visual confirmation evaluating apparatus 1-1 illustrated in FIG. 1 includes an apparatus part provided on the side of a vehicle 10, and an apparatus part provided on the side of a server 20. Wireless communication between the vehicle 10 and the server 20 may be performed between a known communication unit (or interface) provided on the side of the vehicle 10 and a known communication unit (or interface) provided on the side of the server 20. In FIG. 1, the illustration of the communication units (or interfaces), antennas, or the like will be omitted for the sake of convenience. In this embodiment, the vehicle 10 may be an automobile, for example. However, the vehicle 10 may be a two-wheel vehicle, such as a motorcycle.

The vehicle 10 may include a rear camera 11 to pick up an image from a rear of the vehicle 10, an image storage unit 12, an on-board camera (or dashboard camera) 13 to pick up the face of a driver within the vehicle 10, a head position acquiring unit 14, a line of sight acquiring unit 15, a CAN (Controller Area Network) unit 16, and a CAN data storage unit 17. The image storage unit 12 may store image data visible from the rear of the vehicle 10 and picked up by the rear camera 11. The on-board camera 13 may be formed by one or a plurality of driver monitoring cameras that are provided on a dashboard of the vehicle 10, for example. The on-board camera 13 picks up the head (or face part) of the driver within the vehicle 10. A mounting position of the on-board camera 13 is not limited to a particular position as long as the on-board camera 13 can pickup the head of the driver within the vehicle 10. For example, the mounting position of the on-board camera 13 may be a steering column or the like of the vehicle 10.

The head position acquiring unit 14 may subject the image data of the driver's head picked up by the on-board camera 13 to a known image processing, and compute, by a known method, a three-dimensional position (x, y, z) of the driver's head in a coordinate system using the on-board camera 13 as a reference, in order to output head position data, for example. In a case in which the on-board camera 13 is formed by two cameras, for example, the three-dimensional coordinates of each pixel of the head image may be acquired by a known stereogram process that applies triangulation to the image data, and the positions of the driver's right and left eyes may be computed from the processed image data.

The line of sight acquiring unit 15 may subject the image data of the driver's head picked up by the on-board camera 13 to a known image processing, in a manner similar to the head position acquiring unit 14, and compute, by a known method, a three-dimensional direction vector $(v_x, v_y, v_z)$ of the driver's line of sight in the coordinate system using the on-board camera 13 as the reference, in order to output line-of-sight data, for example. In a case in which the on-board camera 13 is formed by an infrared device (or infrared irradiating device), the direction vector of the driver's line of sight may be computed using a known corneal reflection method, based on a picked up image of infrared ray reflected at the cornea of the driver's eyes, a geometrical relationship between the on-board camera 13 and the infrared ray irradiation, and a model of the human eyeball.

The CAN unit 16 may be a known unit that outputs the CAN data. The CAN data output from the CAN unit 16 may include vehicle velocity data, yaw rate (or angular velocity) data, or the like that are acquired using a known velocity sensor, a known acceleration sensor, or the like. The CAN data output from the CAN unit 16 may be stored in the CAN data storage unit 17.

The image storage unit 12 and the CAN data storage unit 17 within the vehicle 10 may be formed by separate storage units or by a single storage unit.

Functions of at least one of the head position acquiring unit 14 and the line of sight acquiring unit 15 within the vehicle 10 may be performed using or a plurality of processors, such as a CPU (Central Processing Unit). In this case, the processor (or computer) can execute a program to perform the functions of at least one of the head position acquiring unit 14 and the line of sight acquiring unit 15. The program may be stored in a storage unit that forms at least one of the image storage unit 12 and the CAN data storage unit 17, or in a storage unit that is separate from the storage unit or storage units forming the image storage unit 12 and the CAN data storage unit 17. The storage unit that stores the program is not limited to a particular non-transitory computer-readable storage medium, and may be formed by any suitable storage medium including a semiconductor memory device, a magnetic recording medium, an optical recording medium, a magneto-optical recording medium, or the like. In a case in which the non-transitory computer-readable storage medium is formed by a recording medium such as the magnetic recording medium, and the optical recording medium, the storage unit may be formed by a reader and writer (or read and write unit) that writes information to and reads information from the recording medium that is loaded into the reader and writer.

The server 20 may include a storage unit 21, a vehicle position and direction acquiring unit 22, a three-dimensional (hereinafter simply referred to as "3-D") map storage unit 23, a definition data storage unit 24, a viewing information generating unit 25, and a visual confirmation evaluating unit 26. The storage unit 21 may be formed by four storage units separately provided with respect to the image storage unit 12, the head position acquiring unit 14, the line of sight acquiring unit 15, and the CAN data storage unit 17, respectively. Alternatively, the storage unit 21 may be formed by two or more storage units, or by a single storage unit. The 3-D map storage unit 23 stores known 3-D map data representing the map of the real world in which the vehicle 10 travels, by 3-D shape data. In addition, the definition data storage unit 24 stores definition data which will be described later. In a case in which the definition data storage unit 24 stores 3-D map data, the 3-D map storage unit 23 may be omitted.

In the server 20, the image data visible from the rear of the vehicle 10 and picked up by the rear camera 11, line-of-sight data of the driver, and the CAN data that are transmitted from the vehicle 10 may be stored in the storage unit 21.

The vehicle position and direction acquiring unit 22 may acquire position data (hereinafter also referred to as "vehicle position data") of the vehicle 10 on the 3-D map data stored in the 3-D map storage unit 23, and acquire direction data (hereinafter also referred to as "vehicle direction data") of the vehicle 10 based on the image data picked up by the rear camera 11 and stored in the storage unit 21 via the image storage unit 11 and the CAN data output by the CAN unit 16 and stored in the stored in the storage unit 21 via the CAN data storage unit 17. The vehicle position may be acquired using a GPS (Global Positioning System) unit, by acquiring the latitude and longitude of the position of the vehicle 10 based on GPS data. In addition, the vehicle direction may be acquired from time integration of vehicle velocity data and yaw rate data included in the CAN data, from a reference point, because the vehicle position from a reference point and the vehicle direction (or vehicle azimuth) from a reference direction (or reference azimuth) at an arbitrary time may be acquired from the time integration.

On the other hand, in a case in which the vehicle position and the vehicle direction are to be acquired with a high accuracy, the image data picked up by an on-board camera that picks up the image outside the vehicle 10, such as the rear camera 11, for example, may be used. Of course, in a case in which the on-board camera 13 is provided to pick up the image in front of the vehicle 10, the image data picked up by the on-board camera 13 may be used to acquire the vehicle position and the vehicle direction with a high accuracy.

Figure 2:
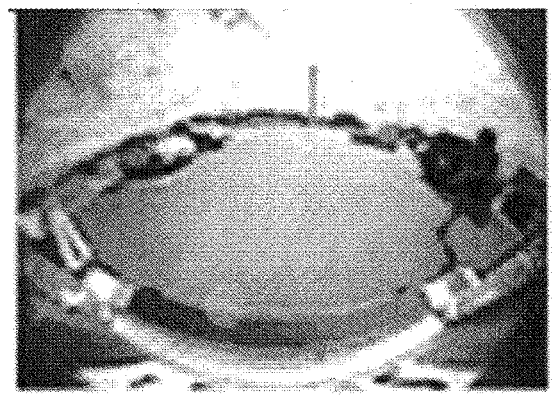
FIG. 2 is a diagram illustrating an example of an image picked up by a rear camera.
Figure 3:
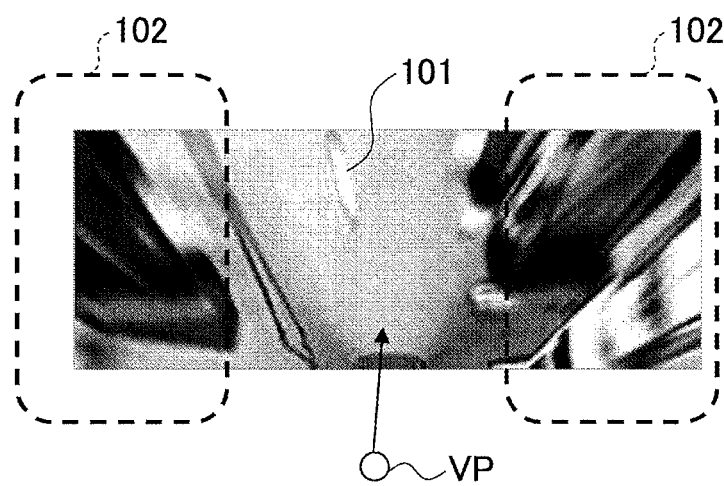
FIG. 3 is a diagram illustrating an example of a viewing point converted image.

The rear camera 11 may pick up the image in a relatively wide angular range by using a fisheye lens or the like, for example, however, the image picked up by the rear camera 11 becomes distorted as illustrated in FIG. 2 when compared to the actual image. For this reason, the picked up image illustrated in FIG. 2 may be converted, by a viewing point conversion, into a viewing point converted image illustrated in FIG. 3 that is viewed from a viewing point (or observation point) located above a road surface and appears as if the picked up image were viewed from the viewing point located immediately above the road surface. However, in the viewing point converted image, 3-D object regions 102, such as buildings located on both sides of the road, become distorted as illustrated by dotted lines surrounding the distorted regions. In FIG. 3, a reference numeral 101 denotes a road surface region (or planar region), VP denotes a virtual position of the rear camera 11, and an arrow extending from the position VP indicates a virtual direction of the rear camera 11.

Amongst the viewing point converted images created based on the images picked up by the rear camera 11, it is known in principle that the viewing point converted images at two successive points in time satisfactorily match in the road surface region 101. Hence, overlapping parts of the viewing point converted images at two consecutive points in time may be merged by subjecting at least one of the two viewing point converted images to a translation T and a rotation R, that is, to an operation $\theta=\{T, R\}$, for example, in order to create a series of road images (so-called road orthographic images). The translation and rotation operation $\theta=\{T, R\}$ may perform a known image processing (that is, a computation process) utilizing the least squares method or the like, for example, so that the overlapping viewing point converted images satisfactorily match. The method itself for creating the road orthographic images in such a manner is known.

Figure 4A:
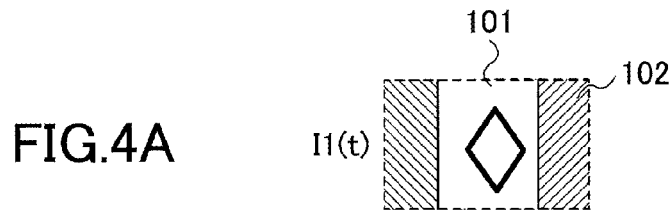
FIGS. 4A, 4B, and 4C are diagrams schematically illustrating examples of the viewing point converted images at consecutive points in time.
Figure 4B:
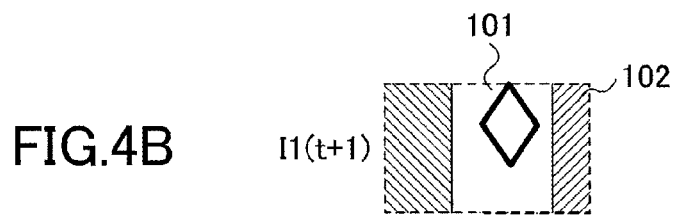
Figure 4C:
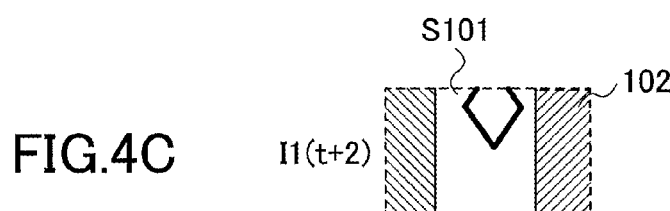

FIGS. 4A, 4B, and 4C are diagrams schematically illustrating examples of the viewing point converted images at consecutive points in time. FIG. 4A illustrates a viewing point converted image $I1(t)$ at a time t, FIG. 4B illustrates a viewing point converted image $I1(t+1)$ at a time t+1, and FIG. 4C illustrates a viewing point converted image $I1(t+2)$ at a time t+2. A diamond shape within the road surface region 101 is a road sign provided on the road and indicating that a pedestrian crossing or a bicycle crossing is located ahead on this road. In this example, the diamond-shaped road signs are utilized to satisfactorily match the viewing point converted images at the consecutive points in time.

Figure 5A:
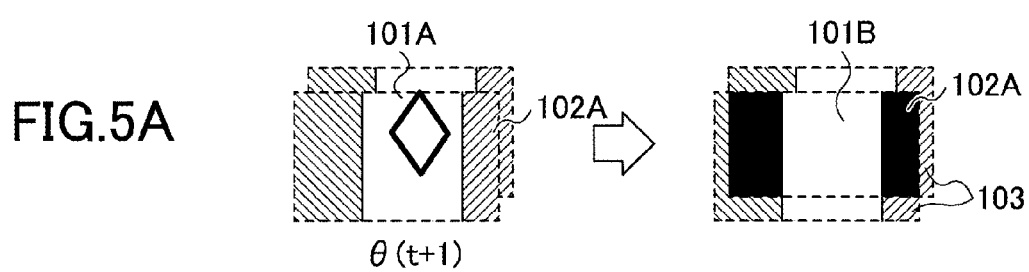
FIGS. 5A and 5B are diagrams for explaining a state in which the viewing point converted images at the consecutive points in time satisfactorily match in a road surface region.
Figure 5B:
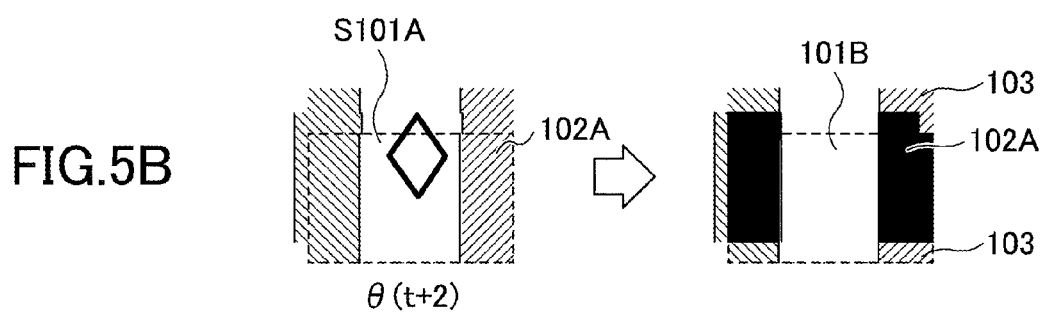

FIGS. 5A and 5B are diagrams for explaining a state in which the viewing point converted images at the consecutive points in time satisfactorily match in the road surface region.

FIG. 5A illustrates a case in which the road orthographic image is created by overlapping the viewing point converted image I1(t+1) at the time t+1 on the viewing point converted image I1(t) at the time t, and subjecting the viewing point converted image I1(t+1), for example, to the translation and rotation operation θ(t+1), in order to merge the overlapping parts of two viewing point converted images. In this case, by performing the translation and rotation operation θ(t+1), the road surface regions of the viewing point converted images I1(t) and I1(t+1) at the times t and t+1, respectively, satisfactorily match as indicated by a reference numeral 101A, however, a 3D region 102A indicated by hatchings do not match. The right part of FIG. 5A illustrates a difference image between the viewing point converted images I1(t) and I1(t+1) at the times t and t+1, and a black part 102A indicates a 3-D object region such as a wall, a white part 101B indicates a road surface region, and a hatching part 103 indicates a non-processed region that is not discriminated as the 3-D object region.

On the other hand, FIG. 5B illustrates a case in which the road orthographic image is created by overlapping the viewing point converted image I(t+2) at the time t+2 on the overlapped viewing point converted images I(t) and I1(t+1) at the times t and t+1, and subjecting the viewing point converted image I1(t+2) to the translation and rotation operation θ(t+2), in order to automatically merge the overlapping parts of two images. In this case, by performing the translation and rotation operation θ(t+2), the road surface regions of the viewing point converted images I1(t), I1(t+1), and I1(t+3) at the times t, t+1, and t+2, respectively, satisfactorily match as indicated by the reference numeral 101A, however, the 3D region 102A indicated by hatchings do not match. The right part of FIG. 5B illustrates a difference image amongst the viewing point converted images I1(t), I1(t+1), and I1(t+2) at the times t, t+1, and t+2, and the black part 102A indicates a 3-D object region such as the wall, the white part 101B indicates a road surface region, and the hatching part 103 indicates a non-processed region that is not discriminated as the 3-D object region.

When the time-adjacent viewing point converted images at consecutive times ti (i=1, 2, ...) and ti+1 (that is, consecutive points in time) are overlapped, the 3-D object regions do not match. Accordingly, the region in which a difference value of the viewing point converted images at the consecutive points in time is less than a predetermined value may be extracted as the road surface region (for example, a binary image data value is "1"), and the region in which the difference value is greater than or equal to the predetermined value may be extracted as the 3-D object region (for example, the binary image data value is "0"). In addition, in the road orthographic image, an intersection shape may be extracted as the difference image (or difference road orthographic image).

The translation and rotation operation θ={T, R} may perform the computation process by using motion information, such as the vehicle velocity data and the yaw rate of the vehicle 10 included in the CAN data output from the CAN unit 16, that is converted into the scale of the viewing point converted image, together with the image processing.

In this example, it is assumed for the sake of convenience that the road surface and the 3-D object are represented by polygon data in the 3-D map data. In a case in which the position of the road region is represented by a plane of z=0 in the xyz coordinate system, the road shape existing in the 3-D map data may be extracted as an image by extracting an intersecting curve between this plane of z=0 and a plane at a predetermined height. In addition, it is assumed that the 3-D map data includes a center position of the intersection and reference direction information. An image of the road surface region may be created, in which a closed region including the center position of the intersection has the binary image data value "1" and other regions have the binary image data value "0", and this image of the road surface region may be used as an intersection template.

Next, a magnification (enlarge or reduce) s, the translation T and the rotation R, that is, the operation θ={s, T, R}, may be performed on the road surface region (for example, the intersection template) existing in the 3-D map data stored in the 3-D map storage unit 23, in order to perform a matching process to match the road surface region to the difference road orthographic image, as illustrated in FIGS. 6A through 6C. The magnification s and the translation T and the rotation R are examples of the image transformation process (or image processing). A parameter θ of the magnification s, translation T and rotation R, that is, the operation θ={s, T, R}, may be computed by performing a known image processing utilizing the least squares method or the like, for example, so that the road surface regions of the overlapping intersection template and difference road orthographic image overlap. FIGS. 6A, 6B, and 6C are diagrams for explaining an example of overlapping the intersection template and the difference road orthographic image. FIG. 6A illustrates the difference road orthographic image, FIG. 6B illustrates the intersection template that has been subjected to the operation θ={s, T, R}, and FIG. 6C illustrates an overlapped image of the difference road orthographic image illustrated in FIG. 6A and the intersection template illustrated in FIG. 6B. In FIGS. 6A through 6C, those parts that are substantially the same as those corresponding parts in FIGS. 5A and 5B are designated by the same reference numerals, and a description thereof will be omitted. The intersection template illustrated in FIG. 6B indicates the two-dimensional road shape obtained from the 3-D map data. A reference numeral 201 indicates a road surface region (or planar region) of the intersection template, a reference numeral 202 indicates the 3-D object region of the intersection template, a reference numeral 205 indicates the center position (hereinafter also referred to as "intersection center position") of the intersection within the intersection template, and a reference numeral 206 indicates the reference direction of the intersection within the intersection template.

When overlapping the difference road orthographic image illustrated in FIG. 6A and the intersection template illustrated in FIG. 6B, the difference road orthographic image, for example, may be fixed, and the intersection template may be subjected to the magnification s, translation T and rotation R, that is, the operation θ={s, T, R}, so that the road surface region 101B and the road surface region 201 match, and the 3-D object region 102A and the 3-D object region 202 match. Hence, in the overlapped road orthographic image illustrated in FIG. 6C, 205A becomes the intersection center position transformed using the parameter θ, and 206A becomes the reference direction transformed using the parameter θ.

Next, a virtual position and direction of the rear camera 11 is obtained as illustrated in FIGS. 7A and 7B with respect to each viewing point converted images forming the road orthographic image, with reference to the intersection center position and the reference direction that are transformed using the parameter θ of the magnification s, translation T and rotation R (that is, with reference to the intersection center position 205A and the reference direction 206A in the overlapped road orthographic image).

FIGS. 7A and 7B are diagrams for explaining an example of a process to compute the vehicle position and the vehicle direction from virtual position and direction of the rear camera. FIG. 7A illustrates the overlapped road orthographic image, and FIG. 7B illustrates the intersection template that is computed from the overlapped orthographic image illustrated in FIG. 7A. In FIG. 7A, VP denotes a virtual position of the rear camera 11, an arrow extending from the position VP indicates a virtual direction from the rear camera 11, a rectangular region indicated by a dotted line indicates an image pickup region of the rear camera 11 from a virtual position VPv, and a bold solid line L1 indicates a virtual moving locus of the vehicle 10 (or rear camera 11).

The virtual position VP of the rear camera 11 can be uniquely computed from the position of each viewing point converted image, and the direction on the viewing point converted image corresponds to the virtual direction of the rear camera 11. In addition, because the position and direction on each viewing point converted image are the position and direction on the overlapped road orthographic image illustrated in FIG. 7A, the vehicle position (or position of the rear camera 11) and the vehicle direction at the intersection template illustrated in FIG. 7B may be computed by an inverse transform based on the parameter θ of the magnification s, translation T and rotation R. In FIG. 7B, a reference numeral 205B indicates the intersection center position within the intersection template that is obtained by the inverse transform, a reference numeral 206B indicates the reference direction of the intersection within the intersection template that is obtained by the inverse transform, and a bold solid line L2 indicates a moving locus of the vehicle 10 (or rear camera 11).

Figure 8:
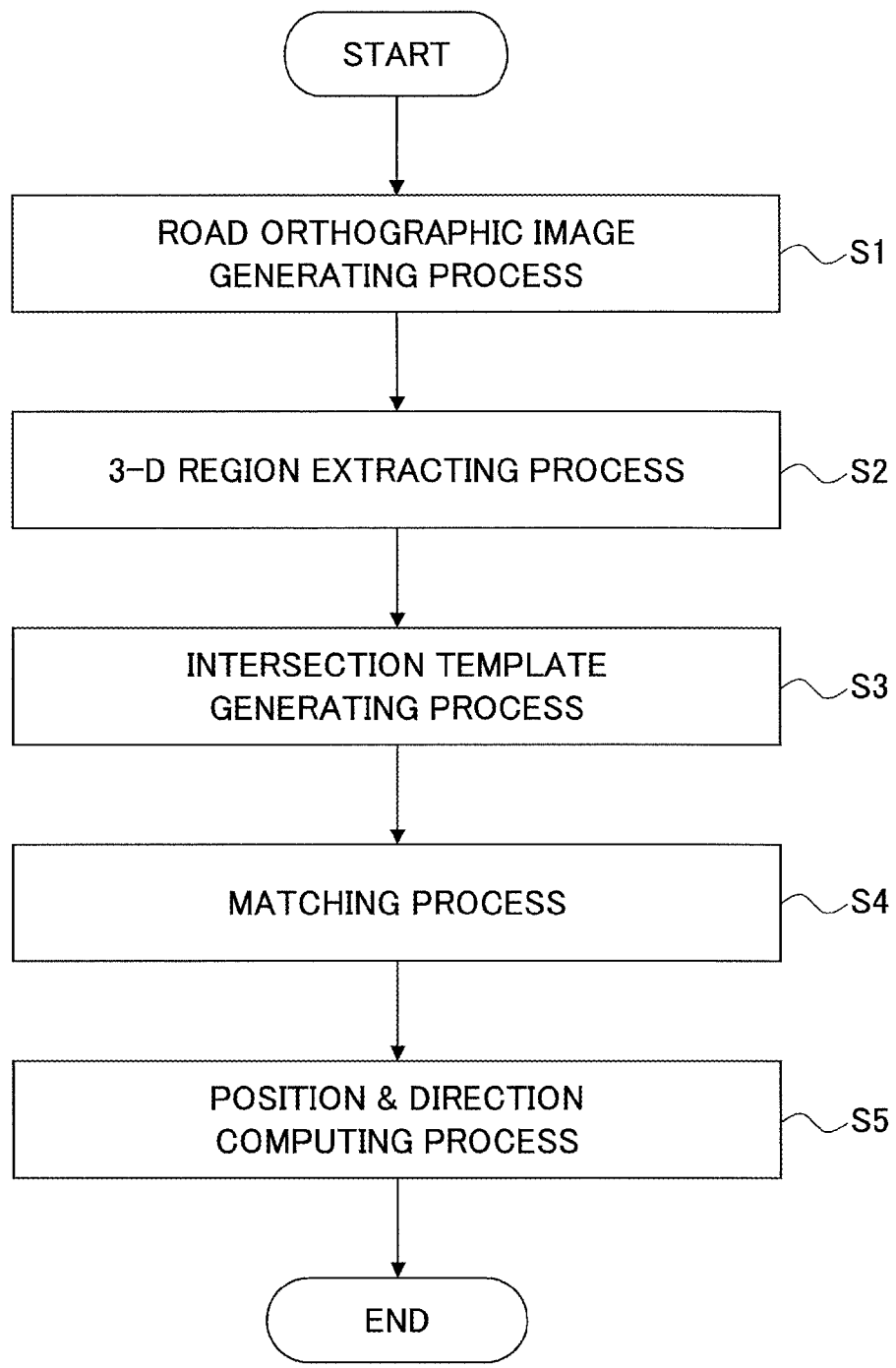
FIG. 8 is a flow chart for explaining an example of a process of a vehicle position and direction acquiring unit.

FIG. 8 is a flow chart for explaining an example of a process of the vehicle position and direction acquiring unit 22. When the process illustrated in FIG. 8 starts, the vehicle position and direction acquiring unit 22, in step S1, reads the image data that is picked up by the rear camera 11 and stored in the storage unit 21 via the image storage unit 12, reads the CAN data that is output from the CAN unit 16 and stored in the storage unit 21 via the CAN data storage unit 17, and performs a road orthographic image generating process based on the image data and the CAN data that are read, in order to overlap the viewing point converted images as described above in conjunction with FIGS. 5A and 5B. The vehicle position and direction acquiring unit 22, in step S2, performs a 3-D region extracting process to extract the 3-D region (that is, difference road orthographic image based on the process results of the road orthographic image generating process, and obtains the difference road orthographic image illustrated in FIG. 6A. The vehicle position and direction acquiring unit 22, in step S3, performs an intersection template generating process to generate the intersection template illustrated in FIG. 6B, based on the 3-D map data stored in the 3-D map storage unit 23 and the definition data stored in the definition data storage unit 24. The vehicle position and direction acquiring unit 22, in step S4, performs a matching process to match the difference road orthographic image and the intersection template as illustrated in FIG. 6C. The vehicle position and direction acquiring unit 22, in step S5, performs a position and direction computing process to compute the vehicle position data that indicates the vehicle position and the vehicle direction data that indicates the vehicle direction according to the method described above in conjunction with FIGS. 7A and 7B, based on the process results of the matching process. The process ends after step S5.

The viewing information generating unit 25 reads, from the storage unit 21, the head position data that is acquired by the head position acquiring unit 14 and stored in the storage unit 21, and the line-of-sight data that is acquired by the line of sight acquiring unit 15 and stored in the storage unit 21. The viewing information generating unit 25 generates unobstructed state information and viewing direction based on the head position data and the line-of-sight data that are read, the vehicle position data and the vehicle direction data acquired by the vehicle position and direction acquiring unit 22, and the 3-D map data stored in the 3-D map storage unit 23.

The viewing information generating unit 25 may include a computing unit to compute the driver's viewing point position and line-of-sight direction. As described above, the vehicle position data and the direction data are virtual data based on the virtual position and the virtual direction of the rear camera 11 in the 3-D map data. On the other hand, the head position data and the line-of-sight data are data on the scale of the read world, and uses, as the reference, the coordinate system of the on-board camera 13 that is set within the vehicle 10. Accordingly, the driver's viewing point position and line-of-sight direction in the 3-D map data can be computed by subjecting the vehicle position data and the vehicle direction data to a correcting process based on a relative position and direction relationship between the rear camera 11 and the on-board camera 13.

The definition data stored in the definition data storage unit 24 may include an ID for identifying the intersection, an intersection reference position, the reference direction, a viewing reference, a confirmation time, an elapsed time, or the like. The definition data defines the viewing reference in the 3-D map data for each intersection identified by the ID, which is an example of an identifier. The viewing reference is the position information of a virtual target that is to be confirmed by the driver when the vehicle 10 enters the intersection, for each road on the right and left directions of the intersection, for example. The position information of the virtual target may be defined as a predetermined distance from the intersection center position along the road shape, for example. The position information of the virtual target may be converted into 3-D position information in the 3-D map data. The viewing direction is defined as the direction from the driver's viewing point position (or head position) towards the viewing reference.

FIGS. 9A, 9B, and 9C are diagrams for explaining the generation of the unobstructed state information and the viewing direction information. In FIGS. 9A through 9C, a road 51 and a road 52 intersect at an intersection 50, and the illustration of the vehicle 10 is omitted. An effective confirmation range 31 in which the roads on the right and left are confirmable when the driver within the vehicle 10 views from the head position 30 towards a confirmation reference direction (in this example, a direction in which the road 52 extends), is 50 (deg) in a state illustrated in FIG. 9A, 100 (deg) in a state illustrated in FIG. 9B, and 220 (deg) in a state illustrated in FIG. 9C. The effective confirmation range 31 varies amongst the states illustrated in FIGS. 9A through 9C, because obstructions 55, such as the walls, trees, buildings, or the like, that obstruct the view of the driver changes as the vehicle enters the intersection 50. The virtual target to be confirmed by the driver when the vehicle 10 enters the intersection 50 is defined as the viewing reference. In this example, it is assumed for the sake of convenience that a right viewing reference 51R and a left viewing reference 51L are defined. The driver cannot visually confirm the right and left viewing references 51R and 51L in the state illustrated in FIG. 9A. The driver can visually confirm only the right viewing reference 51R in the state illustrated in FIG. 9B. The driver can visually confirm both the right and left viewing references 51R and 51L in the state illustrated in FIG. 9C.

The size of the human, bicycle, automobile, or the like may be set with respect to the virtual target. It is possible to evaluate whether the view from the driver's head position (or driver's viewing point position) within the vehicle provides sufficient visibility of the virtual target, by taking into consideration the 3-D shape of the intersection obtained from the 3-D map data. More particularly, amongst straight lines connecting the driver's head position (or viewing point position) and sampling points on the shape of the virtual target, a ratio of the lines intersecting the 3-D data of the intersection is obtained, and the unobstructed state information indicating the unobstructed view state is obtained when the ratio is less than or equal to a predetermined threshold value. In other words, the unobstructed state information is generated using an intersecting line judging process to judge line segments that connect the driver's head position and the viewing references in the 3-D map data and intersect the 3-D polygons existing in the 3-D map data. The unobstructed state is defined as a range of the head position (or viewing point position) from which the driver can visually confirm the viewing references 51R and 51L, that is, as the effective confirmation range 31. In addition, the viewing direction is defined as a direction in which the viewing references 51R and 51L are visible from the driver's head position (or viewing point position).

FIG. 10 is a flow chart for explaining a viewing direction registration process of the viewing information generating unit 25. In FIG. 10, the viewing information generating unit 25, in step S11, acquires viewing point position data from the computing unit described above that computes the driver's viewing point position and line-of-sight direction. The viewing information generating unit 25, in step S12, acquires the viewing reference from the definition data stored in the definition data storage unit 24. The viewing information generating unit 25, in step S13, acquires the 3-D map data stored in the 3-D map storage unit 23. The viewing information generating unit 25, in step S14, judges the unobstructed state, based on the 3-D map data that include the viewing point position data, the viewing reference, and information related to the obstructions 55 on the roads 51 and 52 and at the intersection 50. The viewing information generating unit 25, in step S15, stores a judgment result indicating whether the state is the unobstructed state in a storage unit (not illustrated) within the viewing information generating unit 25, for example, or in the storage unit 21. The viewing information generating unit 25, in step S16, computes the viewing direction in which both the right and left viewing references 51R and 51L are visible from the driver's head position (or viewing point position), as illustrated in FIG. 9C. The viewing information generating unit 25, in step S17, stores the computed viewing direction in the storage unit (not illustrated) within the viewing information generating unit 25, for example, or in the storage unit 21, and the process ends. As a result, information related to the viewing direction and the unobstructed state is registered with respect to the intersection 50 that is a target of the registration.

Results of the viewing direction registration process of the viewing information generating unit 25 may be stored in the storage unit (not illustrated) within the viewing information generating unit 25, for example, or in the storage unit 21. FIG. 11 is a diagram illustrating an example of the results of the viewing direction registration process of the viewing information generating unit 25. In the example illustrated in FIG. 11, the process results include the viewing direction, the unobstructed state, and other attributes if necessary, that are stored with respect to each of times $t_i$, $t_{i+1}$, ... $t_n$ in a table format in the storage unit 21. The unobstructed state is represented by a value "1" to indicate the unobstructed state, and by a value "0" to indicate the obstructed state.

Figure 12:
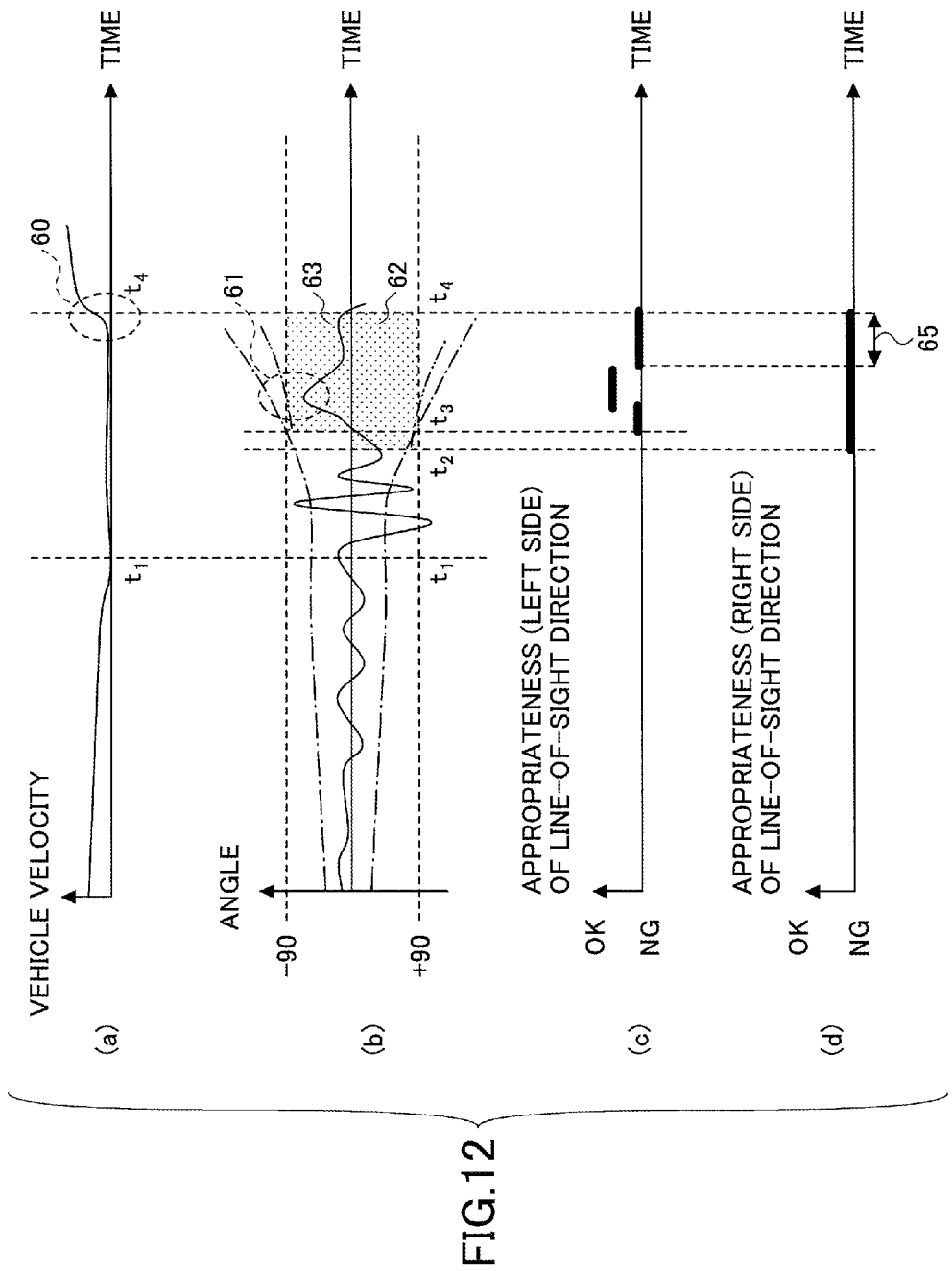
FIG. 12 is a diagram for explaining an example of a line-of-sight direction judging process of the viewing information generating unit.

FIG. 12 is a diagram for explaining an example of a line-of-sight direction judging process of the viewing information generating unit 25. In FIG. 12, the abscissa indicates the time in arbitrary units, (a) illustrates the vehicle velocity of the vehicle 10 in arbitrary units, (b) illustrates the effective confirmation range 31, (c) illustrates the appropriateness (or suitability), "OK" for appropriate (or good) and "NG" for inappropriate (or no good), of the line-of-sight direction towards the left side, and (d) illustrates the appropriateness, "OK" for appropriate (or good) and "NG" for inappropriate (or no good), of the line-of-sight direction towards the right side.

In FIG. 12, $t_1$ denotes a time when entry of the vehicle 10 into the intersection 50 starts, $t_2$ denotes a time when the visual confirmation of the right viewing reference 51R can start (that is, becomes possible), and $t_3$ denotes a time when the visual confirmation of the left viewing reference 51L can start (that is, becomes possible) and the visual confirmation of both the right and left viewing references 51R and 51L can start (that is, becomes possible). In addition, $t_4$ denotes a time (hereinafter also referred to as "moving decision-making time") when acceleration starts as the vehicle 10 passes the intersection 50, that is, the time or timing at which the driver makes the decision to move the vehicle 10 in order to pass the intersection 50. The moving decision-making time $t_4$ may be acquired by judging the rising position of the vehicle velocity from the vehicle velocity data included in the CAN data, for example. In addition, a region 60 illustrated in (a) of FIG. 12 represents a region before and after the moving decision-making time $t_4$ when the vehicle 10 passes the intersection 50.

In FIG. 12 (b), a one-dot chain line indicates the effective confirmation range 31, a solid line indicates the line-of-sight direction, and a two-dot chain line indicates the viewing direction. In addition, a reference numeral 61 denotes a region in which the difference between the line-of-sight direction and the viewing direction is within a predetermined value, a reference numeral 62 denotes a region in which the right viewing reference 51R is visually confirmable, and a reference numeral 63 denotes a region in which the left viewing reference 51L is visually confirmable. In FIGS. 12 (c) and (d), the appropriateness of the line-of-sight direction is judged to be appropriate in a region 65 in which the appropriateness is "OK" for the line-of-sight direction in both the right direction and the right direction.

Figure 13:
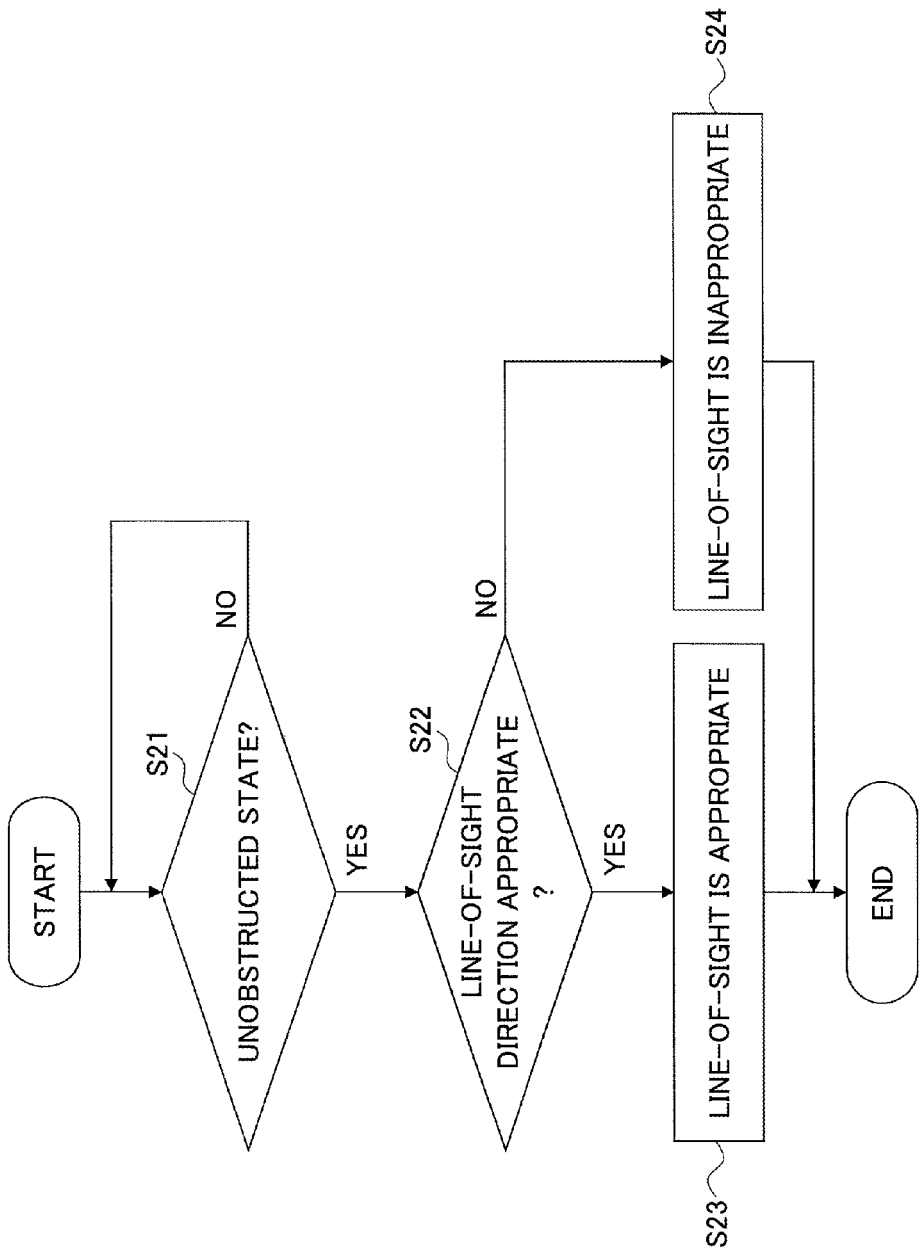
FIG. 13 is a flow chart for explaining an example of the line-of-sight direction judging process of the viewing information generating unit.

FIG. 13 is a flow chart for explaining an example of the line-of-sight direction judging process of the viewing information generating unit 25. In FIG. 13, the viewing information generating unit 25, in step S21, judges whether the driver within the vehicle 10 entering the intersection 50 is in the unobstructed state. In the example illustrated in FIG. 12, the driver assumes the unobstructed state from the time $t_2$. When the judgment result in step S21 is YES, the viewing information generating unit 25, in step S22, judges whether the line-of-sight direction is appropriate. In the example illustrated in FIG. 12, the judgment result in step S22 becomes YES within the region 65 in which the appropriateness is "OK" for the line-of-sight direction in both the right direction and the right direction. When the judgment result in step S22 is YES, the viewing information generating unit 25, in step S23, determines that the line-of-sight direction is appropriate. On the other hand, the judgment result in step S22 becomes NO in regions other than the region 65 in which the appropriateness is "OK" for the line-of-sight direction in both the right direction and the right direction. When the judgment result in step S22 is NO, the viewing information generating unit 25, in step S24, determines that the line-of-sight direction is inappropriate.

Results of the line-of-sight direction judging process of the viewing information generating unit 25 may be stored in the storage unit (not illustrated) within the viewing information generating unit 25, for example, or in the storage unit 21. FIG.

14 is a diagram illustrating an example of the results of the line-of-sight direction judging process of the viewing information generating unit 25. In the example illustrated in FIG. 14, the process results include the line-of-sight direction, the viewing direction, the unobstructed state, and the appropriateness of the line-of-sight direction, that are stored with respect to each of times $t_i, t_{i+1}, \ldots, t_n$ in a table format in the storage unit 21. The unobstructed state is represented by a value "1" to indicate the unobstructed state, and by a value "0" to indicate the obstructed state.

The line-of-sight direction judging process of the viewing information generating unit 25 may be performed with respect to each of two or more viewing references existing in the direction in which the road extends towards the right and left.

The visual confirmation evaluating unit 26 evaluates the appropriateness of the visual confirmation operation (or safety check operation) of the driver by a score value, based on the head position data acquired by the head position acquiring unit 14 and stored in the storage unit 21, the line-of-sight data acquired by the line-of-sight acquiring unit 15 and stored in the storage unit 21, the vehicle position data and the vehicle direction data acquired by the vehicle position and direction acquiring unit 22, the unobstructed state information and the viewing direction information generated by the viewing information generating unit 25, and the definition data stored in the definition data storage unit 24.

Figure 15:
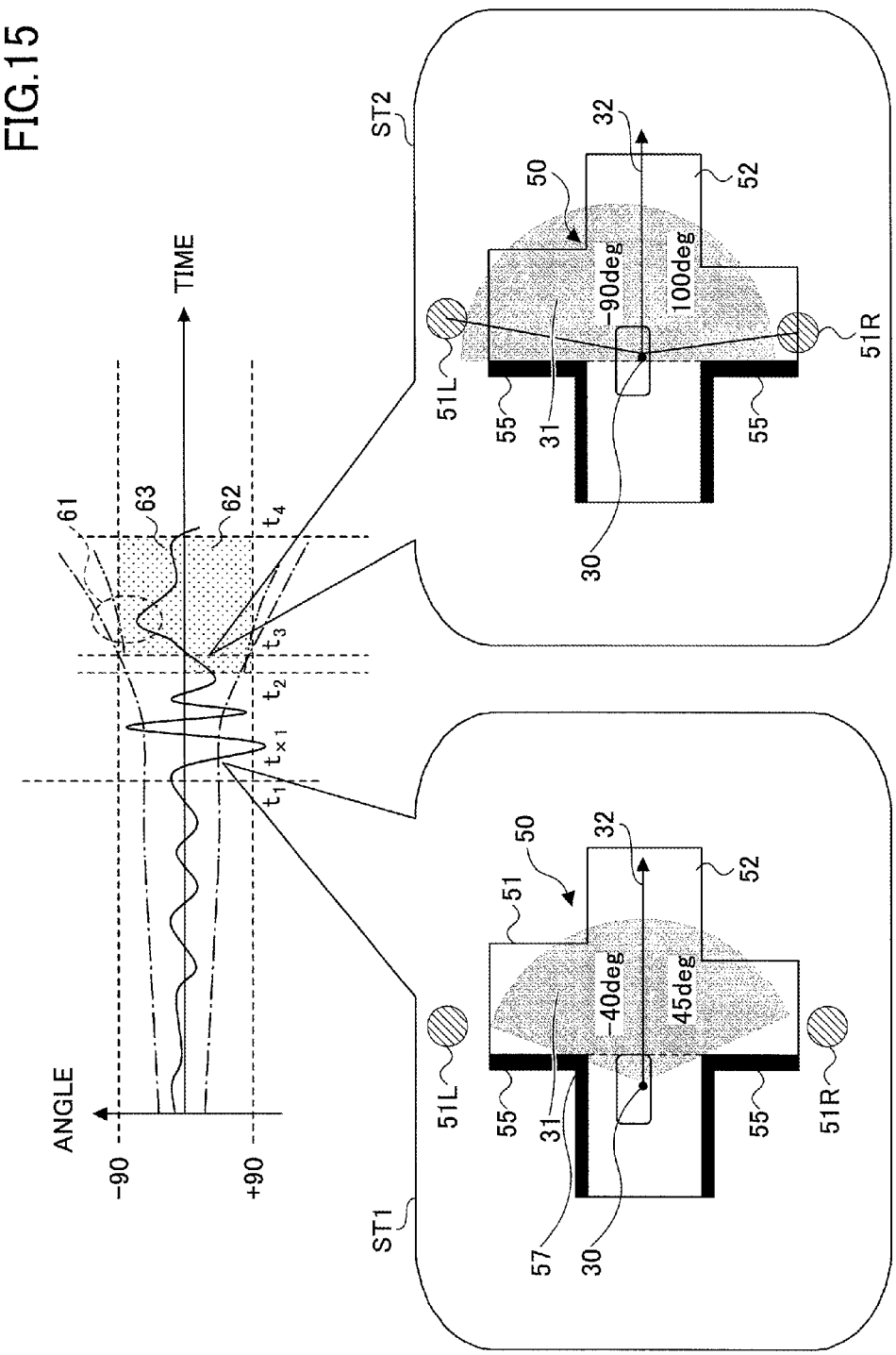
FIG. 15 is a diagram for explaining a process of a visual confirmation evaluating unit.

FIG. 15 is a diagram for explaining a process of the visual confirmation evaluating unit 26. In FIG. 15, an upper part is the same as FIG. 12 (b). A bottom left part of FIG. 15 illustrates an entering state ST1 of the vehicle 10 entering the intersection 50 at a time $t_{x1}$ ($>t_1$) when the vehicle 10 slightly exceeds an entry start position 57 where the entry of the vehicle 10 into the intersection 50 starts. A bottom right part of FIG. 15 illustrates an entering state ST2 of the vehicle 10 entering the intersection 50 at the time $t_3$. In FIG. 15, those parts that are the same as those corresponding parts in FIGS. 9A through 9C and FIG. 12 are designated by the same reference numerals, and a description thereof will be omitted. In the entering state ST1, the driver of the vehicle 10 is still unable to visually confirm the right and left viewing references 51R and 51L. On the other hand, in the entering state ST2, the driver of the vehicle 10 is able to visually confirm the right and left viewing references 51R and 51L.

The line-of-sight data is defined in the coordinate system of the on-board camera 13 that is set within the vehicle 10. Hence, the line-of-sight data indicating the line-of-sight direction of the driver in the 3-D map data may be computed by performing a process similar to the computing unit that computes the viewing point position and the line-of-sight direction in the viewing information generating unit 25. Accordingly, the line-of-sight data, the unobstructed state information, and the viewing direction information in the coordinate system of the 3-D map data may be successively acquired for each of the times as illustrated in FIGS. 14 and 15. The appropriateness of the visual confirmation made by the driver can be evaluated by the store value computed based on such information.

Figure 16:
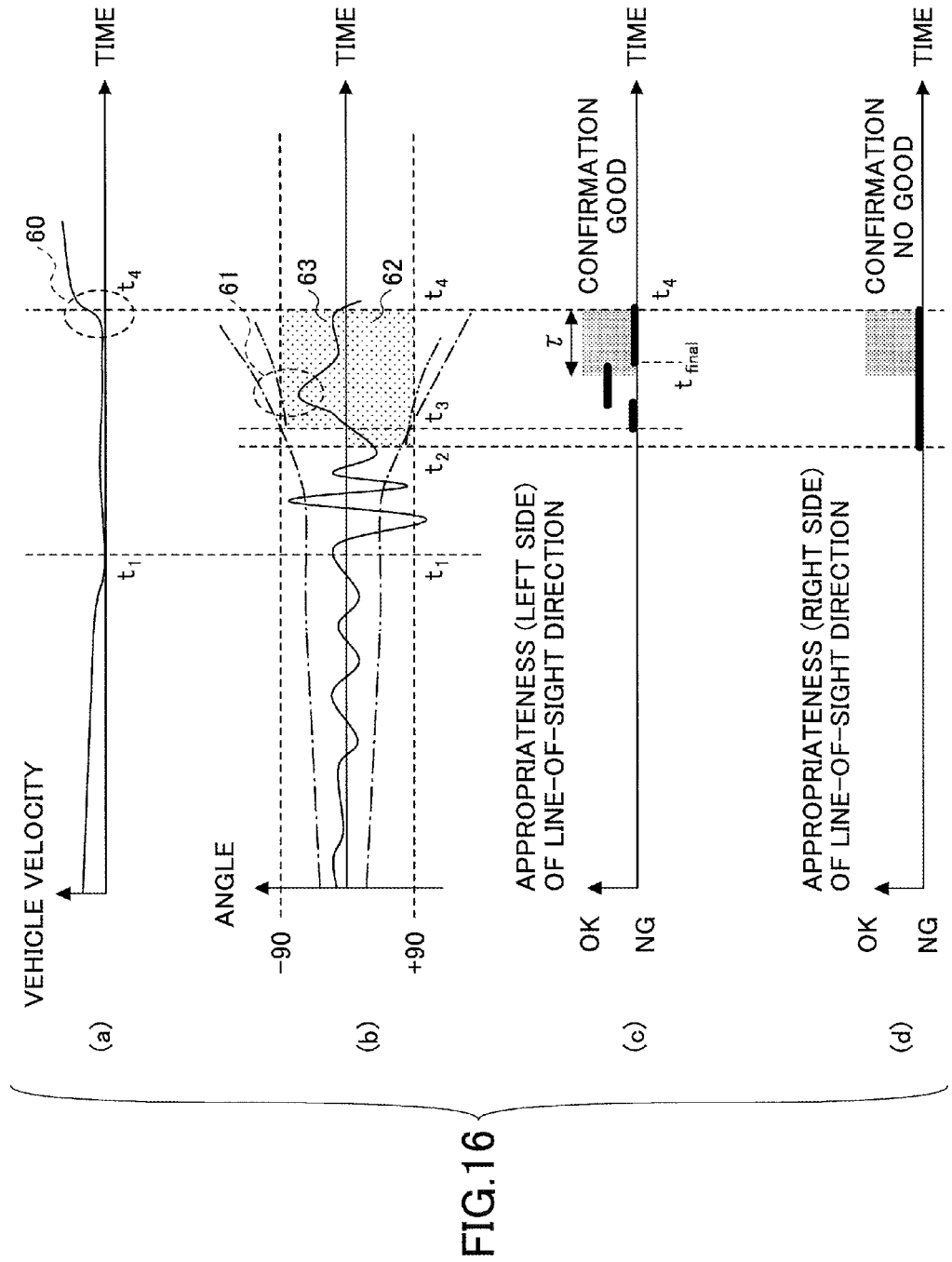
FIG. 16 is a diagram for explaining an example of a confirmation process a visual confirmation evaluating unit.

FIG. 16 is a diagram for explaining an example of a confirmation process the visual confirmation evaluating unit 26. In FIG. 16, the abscissa indicates the time in arbitrary units, (a) illustrates the vehicle velocity of the vehicle 10 in arbitrary units, (b) illustrates the effective confirmation range 31, (c) illustrates the appropriateness (or suitability), "OK" for appropriate (or good) and "NG" for inappropriate (or no good), of the line-of-sight direction towards the left side, and (d) illustrates the appropriateness, "OK" for appropriate (or good) and "NG" for inappropriate (or no good), of the line-of-sight direction towards the right side. In FIG. 16, those parts that are the same as those corresponding parts in FIG. 12 are designated by the same reference numerals, and a description thereof will be omitted.

At a time t, when in the unobstructed state, the appropriateness of a line-of-sight direction Gaze_t is judged. More particularly, the difference between the line-of-sight direction Gaze_t and a viewing direction Dir_t needs to be within a predetermined range Th. When the difference between the line-of-sight direction Gaze_t and the viewing direction Dir_t is within the predetermined range Th, the appropriateness of the line-of-sight direction Gaze_t is determined to be appropriate ("OK"). Assuming that the human central vision (or foveal vision) is ±30 (deg), for example, it is possible to judge whether the driver made an appropriate visual confirmation, by judging whether the viewing direction Dir_t exists in a range of the line-of-sight direction Gaze_t±30 (deg), that is, whether |Dir_t−Gaze_t|=<Th. The predetermined range Th may be set to a value to suit characteristics of the individual driver, characteristics (or features) of the intersection 50, or the like.

Next, a time segment in which the appropriateness of the line-of-sight direction Gaze_t is determined to be appropriate ("OK") by the appropriateness judging is extracted, and an appropriateness of the duration of the time segment is evaluated. More particularly, the confirmation time defined for the intersection 50 is acquired from the definition data stored in the definition data storage unit 24, and a score value SC1 is set to 100 points, for example, when the duration of the time segment in which the appropriateness of the line-of-sight direction Gaze_t is determined to be appropriate ("OK") is greater than or equal to the confirmation time. On the other hand, when the duration of the time segment in which the appropriateness of the line-of-sight direction Gaze_t is determined to be appropriate ("OK") is less than the confirmation time, the score value SC1 is computed from {(duration time)/(confirmation time)}×100, for example. The confirmation time is the time required to make the minimum required visual confirmation (or safety check), for example, at the position where the intersection 50 is visible from the driver. The confirmation time may be set to a value to suit the characteristics of the individual driver or the like.

Next, the moving decision-making time $t_4$ is computed. The moving decision-making time $t_4$ may be acquired by evaluating the vehicle velocity data included in the CAN data stored in the storage unit 21, and judging the rising position of the vehicle velocity. Next, a final confirmation time (or confirmation complete time) $t_{final}$ is acquired for a last time segment in which the appropriateness of the line-of-sight direction Gaze_t is determined to be appropriate. The last time segment is the time segment in which the appropriateness of the line-of-sight direction Gaze_t is determined to be appropriate, and which appears first when going back in time from the moving decision-making time $t_4$.

Next, the appropriateness of the final confirmation timing may be evaluated to be appropriate when $|t_4-t_{final}|$ is less than or equal to an elapsed time (or predetermined threshold value) τ that is included in the definition data stored in the definition data storage unit 24. The elapsed time τ is a maximum delay time of the time or timing at which the driver makes the decision to move the vehicle 10. This elapsed time τ may be set to a value to suit the characteristics of the individual driver, the characteristics of the intersection 50, or the like. In this example, the score value SC2 is computed according to a score function that regards the driver's driving to be better and safer as the difference $|t_4-t_{final}|$ between the final confirmation time $t_{final}$ and the moving decision-making time $t_4$ becomes smaller, and that the driver's driving is poorer and more unsafe as the difference $|t_4-t_{final}|$ exceeds the elapsed time τ by a larger amount.

Finally, a score value SC is computed by combining the score value SC1 and the score value SC2. For example, the score value SC may be computed from SC=k1×SC1+k2×SC2, where k1=0.3 and k2=0.7, for example.

Figure 17:
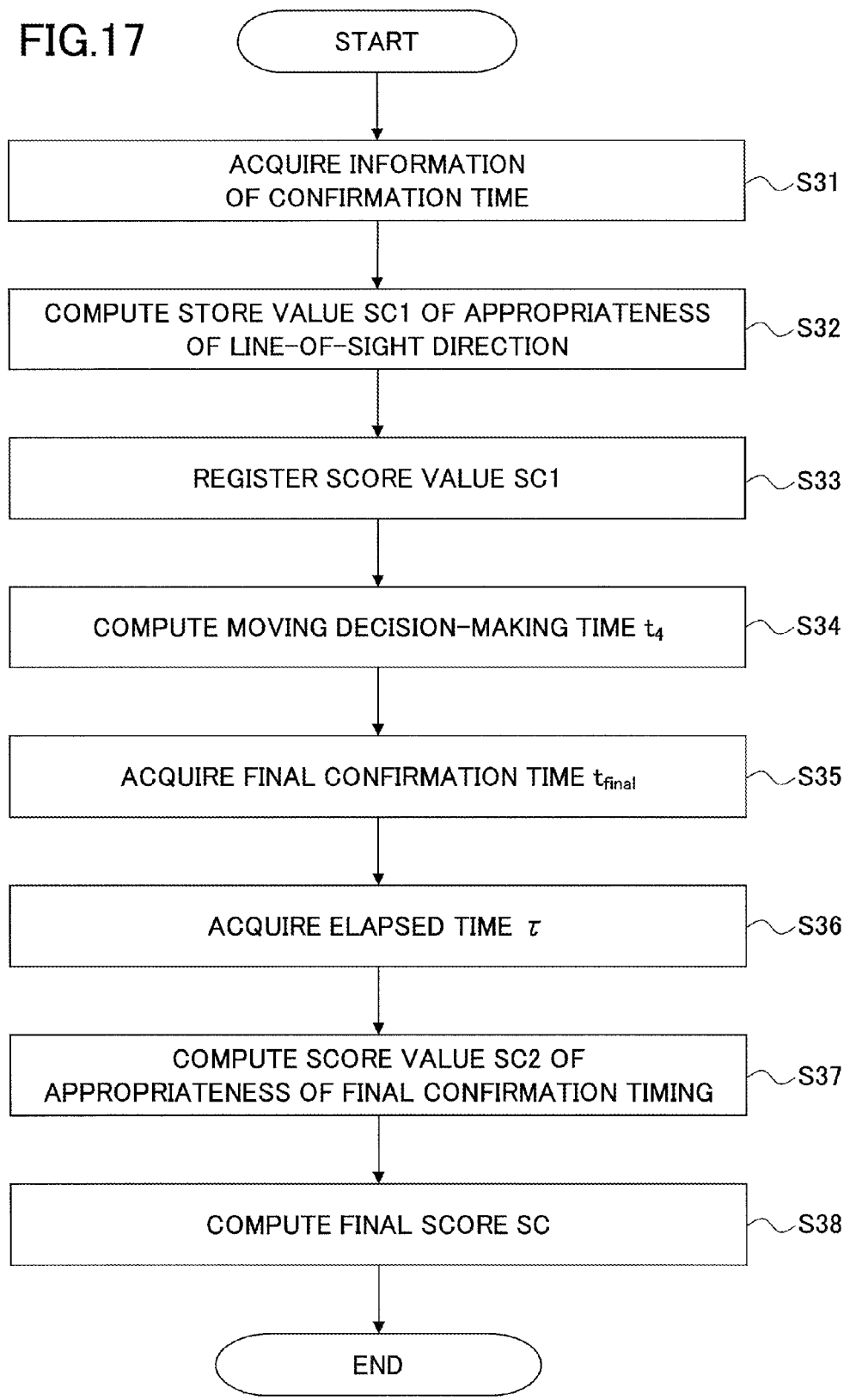
FIG. 17 is a flow chart for explaining an example of the confirmation process of the visual confirmation evaluating unit.

FIG. 17 is a flow chart for explaining an example of the confirmation process of the visual confirmation evaluating unit 26. In FIG. 17, the visual confirmation evaluating unit 26, in step S31, acquires the confirmation time defined for the intersection 50 from the definition data stored in the definition data storage unit 24. The visual confirmation evaluating unit 26, in step S32, computes the score value SC1 of the appropriateness of the line-of-sight direction. More particularly, the score value SC1 is set to 100 points when the duration time of the time segment in which the appropriateness of the line-of-sight direction Gaze_t is appropriate is the confirmation time or longer, and computes the score value SC1 from {(duration time)/(confirmation time)}×100, for example, when the duration time of the time segment in which the appropriateness of the line-of-sight direction Gaze_t is appropriate is shorter than the confirmation time. The visual confirmation evaluating unit 26, in step S33, registers the computed score value SC1 by storing the score value SC1 into the storage unit (not illustrated) within the visual confirmation evaluating unit 26 or the storage unit 21.

The visual confirmation evaluating unit 26, in step S34, computes the moving decision-making time $t_4$ in the manner described above. The visual confirmation evaluating unit 26, in step S35, acquires the final confirmation time $t_{final}$ for the last time segment in which the appropriateness of the line-of-sight direction Gaze_t is determined to be appropriate, where the last time segment is the time segment in which the appropriateness of the line-of-sight direction Gaze_t is determined to be appropriate, and which appears first when going back in time from the moving decision-making time $t_4$. The visual confirmation evaluating unit 26, in step S36, acquires the elapsed time τ that is included in the definition data stored in the definition data storage unit 24.

Figures 18, 19:
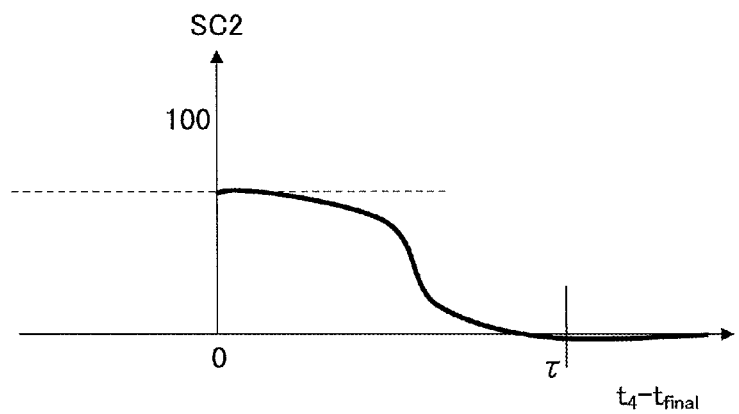
FIG. 18 is a diagram for explaining a score value SC2.
FIG. 19 is a diagram illustrating an example of results of the confirmation process of the visual confirmation evaluating unit.

The visual confirmation evaluating unit 26, in step S37, computes the score value SC2 according to the score function that regards the driver's driving to be better and safer as the difference $|t_4-t_{final}|$ between the final confirmation time t and the moving decision-making time $t_4$ becomes smaller, and that the driver's driving is poorer and more unsafe as the difference $|t_4-t_{final}|$ exceeds the elapsed time τ by a larger amount. FIG. 18 is a diagram for explaining the score value SC2. In FIG. 18, the ordinate indicates the score value SC2, and the abscissa indicates the difference $t_4-t_{final}$. Next, the visual confirmation evaluating unit 26, in step S38, computes the combined score value SC from from SC=k1×SC1+k2×SC2, for example, and the process ends.

FIG. 19 is a diagram illustrating an example of results of the confirmation process of the visual confirmation evaluating unit 26. In the example illustrated in FIG. 19, the process results include the duration time and the score value SC that are stored with respect to each of time segments 1, 2, ..., k in a table format in the storage unit 21.

In the example illustrated in FIG. 15, if the visual confirmation were evaluated based solely on the movement of the driver's head, for example, as in the case of the conventional technique, the visual confirmation at each peak detected at the time $t_1$ and thereafter would be judged to be appropriate. On the other hand, when the visual confirmation made by the driver is evaluated by the score value SC as in the case of the embodiment described above, the visual confirmation is not judged to be appropriate until the time $t_3$ and thereafter. In addition, the embodiment described above does not judge the visual confirmation to be appropriate unless the driver makes a visual confirmation that satisfies a predetermined condition within the elapsed time τ going back in time from the moving decision-making time $t_4$. For this reason, when compared to the conventional technique, the embodiment can more accurately evaluate the appropriateness of the driver's visual confirmation operation.

The score value SC may be computed with respect to each of two or more viewing references existing in the direction in which the road extends towards the right and left, and the score value computed for each viewing reference may be combined to obtain the final score value.

At least one function of the vehicle position and direction acquiring unit 22, the viewing information generating unit 25, and the visual confirmation evaluating unit 26 of the server 20 may be performed using or or a plurality of processors, such as a CPU. In this case, the processor (or computer) can execute a program to perform the functions of at least one of the vehicle position and direction acquiring unit 22, the viewing information generating unit 25, and the visual confirmation evaluating unit 26. The program may be stored in a storage unit that forms the image storage unit 21, or in a storage unit that is separate from the storage unit 21. The storage unit that stores the program is not limited to a particular non-transitory computer-readable storage medium.

According to the first embodiment, the process having a relatively large load is performed on the side of the server 20, and thus, the load on the processor on the side of the vehicle 10 can be reduced.

Second Embodiment

Figure 20:
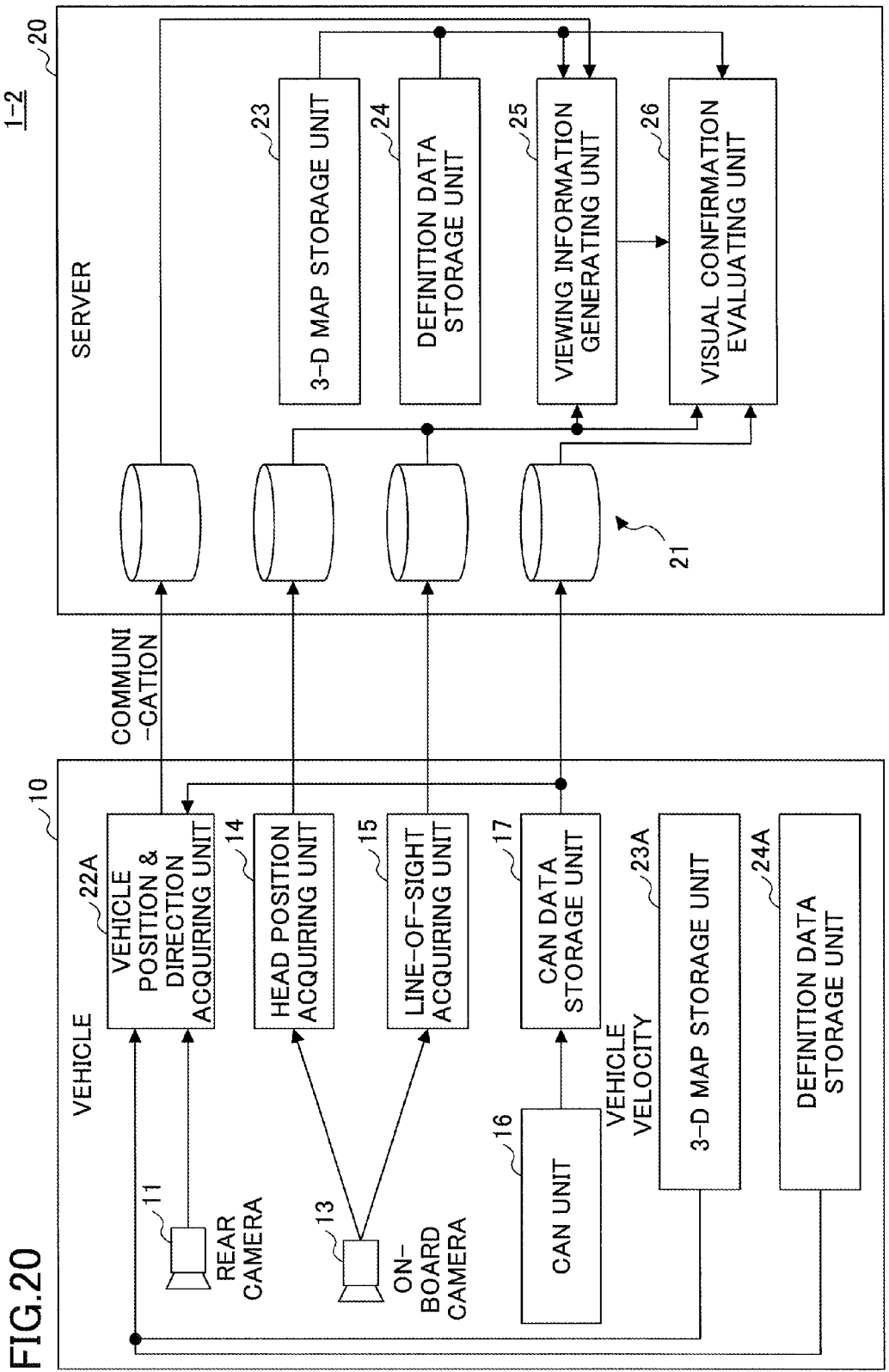
FIG. 20 is a block diagram illustrating an example of the visual confirmation evaluating apparatus in a second embodiment.

FIG. 20 is a block diagram illustrating an example of the visual confirmation evaluating apparatus in a second embodiment. In FIG. 20, those parts that are the same as those corresponding parts in FIG. 1 are designated by the same reference numerals, and a description thereof will be omitted. In the second embodiment, a vehicle position and direction acquiring unit 22A, a 3-D map storage unit 23A, and a definition data storage unit 24A are provided on the side of the vehicle 10, and a part of the operation of the server 20 of the first embodiment is performed on the side of the vehicle 10. However, the operation of a visual confirmation evaluating apparatus 1-2 as a whole is basically the same as that of the first embodiment described above. The vehicle position and direction acquiring unit 22A, the 3-D map storage unit 23A, and the definition data storage unit 24A operate similarly to the vehicle position and direction acquiring unit 22, the 3-D map storage unit 23, and the definition data storage unit 24 of the first embodiment, respectively.

According to the second embodiment, the load of the process can be distributed between the vehicle 10 and the server 20.

Third Embodiment

Figure 21:
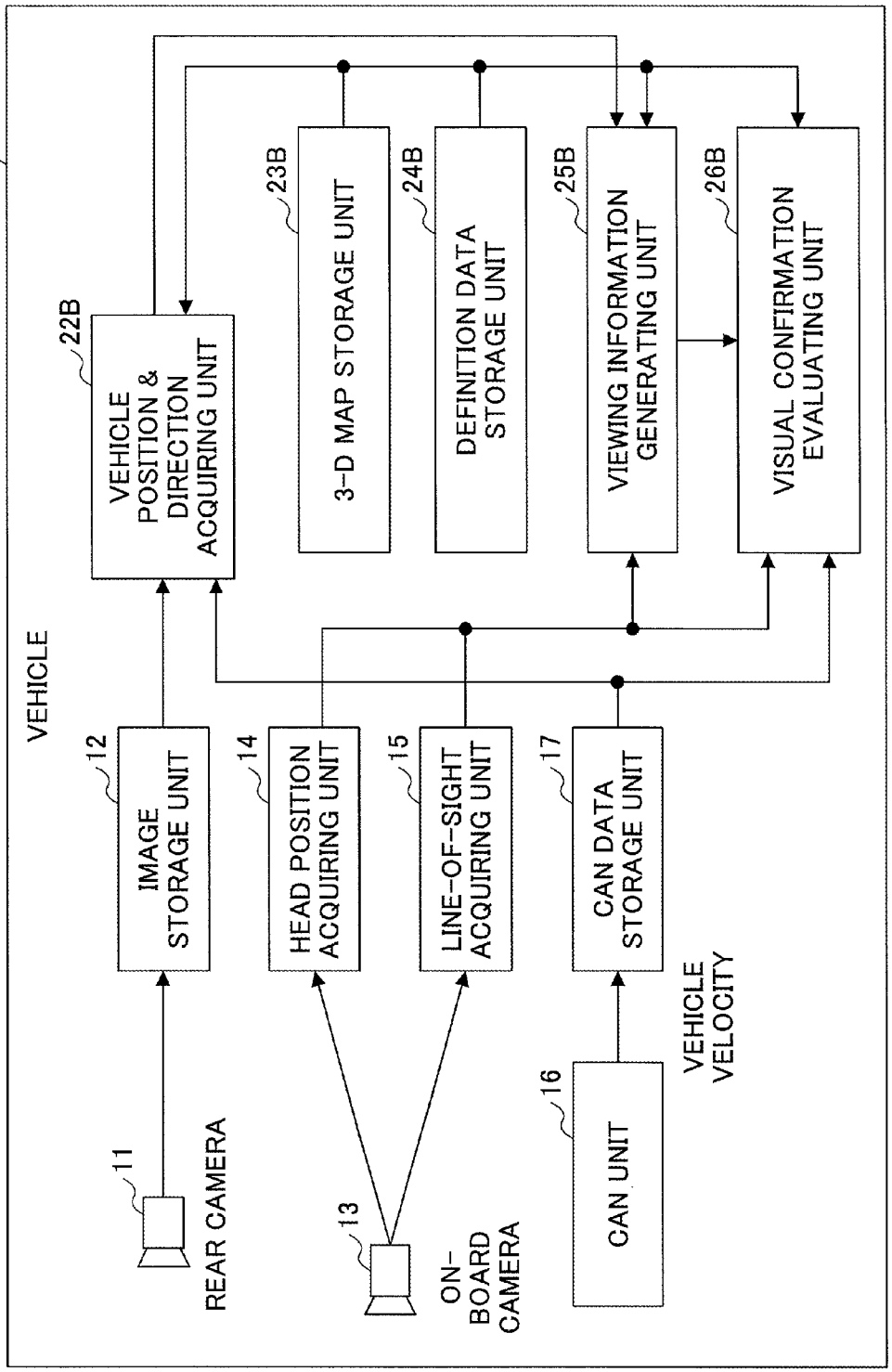
FIG. 21 is a block diagram illustrating an example of the visual confirmation evaluating apparatus in a third embodiment.

FIG. 21 is a block diagram illustrating an example of the visual confirmation evaluating apparatus in a third embodiment. In FIG. 21, those parts that are the same as those corresponding parts in FIG. 1 are designated by the same reference numerals, and a description thereof will be omitted. In the third embodiment, the operation of the server 20 of the first embodiment is performed on the side of the vehicle 10. However, the operation of a visual confirmation evaluating apparatus 1-3 as a whole is basically the same as that of the first embodiment described above. In the third embodiment, a vehicle position and direction acquiring unit 22B, a 3-D map storage unit 23B, a definition data storage unit 24B, a viewing information generating unit 25B, and a visual confirmation evaluating unit 26B are provided on the side of the vehicle 10. The vehicle position and direction acquiring unit 22B, the 3-D map storage unit 23B, the definition data storage unit 24B, the viewing information generating unit 25B, and the visual confirmation evaluating unit 26B operate similarly to the vehicle position and direction acquiring unit 22, the 3-D map storage unit 23, the definition data storage unit 24, the viewing information generating unit 25, and the visual confirmation evaluating unit 26 of the first embodiment, respectively. In the third embodiment, the storage unit 21 illustrated in FIG. 1 may be omitted.

According to the third embodiment, the entire process is performed on the side of the vehicle 10, and thus, the server 20 may be omitted.

In each of the embodiments described above, the rear camera 11, the image storage unit 12, the storage unit 21, and the vehicle position and direction acquiring units 22, 22A, and 22B may form a vehicle position and direction acquiring means (or module or unit) that acquires the position data and the direction data of the vehicle 10. The on-board camera 13 and the head position acquiring unit 14 may form a head position acquiring means (or module or unit) that acquires the head position data (or viewing point position data) of the driver. The on-board camera 13 and the line-of-sight acquiring unit 15 may form a line-of-sight acquiring means (or module or unit) that acquires the line-of-sight data of the driver. The CAN apparatus 16 may form a vehicle velocity acquiring means (or module or unit) that acquires the vehicle velocity data of the vehicle 10.

In addition, in each of the embodiments described above, when the visual confirmation operation is evaluated to be inappropriate, a warning may be output to the driver, for example. Alternatively, the results of evaluating the visual confirmation operation may be output to a collision preventing system or the like that reduces the vehicle velocity or stops the vehicle in order to avoid a collision, for example.

According to each of the embodiments described above, it is possible to accurately evaluate the appropriateness of the driver's visual confirmation operation (or safety check operation).

Although the embodiments are numbered with, for example, "first," "second," or "third," the ordinal numbers do not imply priorities of the embodiments. Many other variations and modifications will be apparent to those skilled in the art.

All examples and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification relate to a showing of the superiority and inferiority of the invention. Although the embodiments of the present invention have been described in detail, it should be understood that the various changes, substitutions, and alterations could be made hereto without departing from the spirit and scope of the invention.

What is claimed is:

1. A visual confirmation evaluating apparatus comprising:
a head position acquiring unit configured to acquire head position data indicating a head position of a driver within a vehicle;
a line-of-sight acquiring unit configured to acquire line-of-sight data of the driver;
a velocity acquiring unit configured to acquire velocity data of the vehicle;
a storage unit configured to store three-dimensional map data representing a map of a real world in which the vehicle travels by three-dimensional shape data, and definition data including an identifier to identify each of intersections, a viewing reference, a confirmation time and an elapsed time;
wherein the definition data define the viewing reference in the three-dimensional map data for each of the intersections identified by the identifier, and the viewing reference is position information of a virtual target that is to be confirmed by the driver when the vehicle enters each of the intersections for each road on right and left directions of each of the intersections;
wherein the confirmation time indicates a time required by the driver to make a visual confirmation that is to be made from a position where each of the intersections is visible,
wherein the elapsed time indicates a maximum delay time of a timing at which the driver makes a decision to move the vehicle,
a position and direction acquiring unit configured to acquire position data and direction data indicating a position and a direction of the vehicle in the three-dimensional map data;
a viewing information generating unit configured to generate viewing direction information indicating a direction towards the viewing reference from the head position of the driver indicated by the head position data, and unobstructed state information indicating a state in which the viewing reference is visible from the driver, based on the head position data, the line-of-sight data, the vehicle position data, the direction data, the definition data and the three-dimensional map data; and
a visual confirmation evaluating unit configured to evaluate an appropriateness of a visual confirmation operation of the driver, based on the head position data, the line-of-sight data, the vehicle position data, the direction data, the definition data, the unobstructed state information and the viewing direction information.

2. The visual confirmation evaluating apparatus as claimed in claim 1,
wherein the position and direction acquiring unit includes an on-board camera provided in the vehicle and configured to pick up an image of an outside of the vehicle,
wherein the position and direction acquiring unit performs a process including
generating a road orthographic image that distinguishes a road surface region from other regions, from the image picked up by the on-board camera;
generating an intersection template having a shape of the road surface region, from the three-dimensional map data;
computing a parameter of an image transformation process that matches the road orthographic image and the intersection template; and
computing the vehicle position data and the direction data indicating the position and the direction of the vehicle on the three-dimensional map data, respectively, by computing the position and the direction of the vehicle on the road orthographic image and performing an inverse transform based on the parameter.

3. The visual confirmation evaluating apparatus as claimed in claim 1, wherein the view information generating unit performs a process including computing the head position and the line-of-sight direction of the driver in the three-dimensional map data, based on the position data and the direction data of the vehicle in the three-dimensional map data acquired by the position and direction acquiring unit, the head position data and the line-of-sight data; and generating the unobstructed state information using an intersecting line judging process to judge a line segment that connects the head position of the driver and the viewing reference in the three-dimensional map data and intersects the three-dimensional polygons existing in the three-dimensional map data.

4. The visual confirmation evaluating apparatus as claimed in claim 1, wherein the visual confirmation evaluating unit judges, when the unobstructed state information generated by the viewing information generating unit indicates that the head position is in a range in which the viewing reference is visible from the driver, an appropriateness of the line-of-sight direction by comparing the line-of-sight direction of the driver and the viewing direction information in the three-dimensional map data, and judges the line-of-sight direction to be appropriate when a difference between the compared line-of-sight direction and the viewing direction information is within a predetermined range.

5. The visual confirmation evaluating apparatus as claimed in claim 4, wherein the visual confirmation evaluating unit evaluates the appropriateness of the visual confirmation operation by evaluating a duration in which the appropriateness of the line-of-sight direction is judged to be appropriate.

6. The visual confirmation evaluating apparatus as claimed in claim 4, wherein the visual confirmation evaluating unit performs a process including extracting a time segment corresponding to a duration in which the appropriateness of the line-of-sight direction is judged to be appropriate;

computing a start time at which an acceleration of the vehicle is to start in order to pass each of the intersections, based on the velocity data acquired by the velocity acquiring unit;

extracting a final confirmation time of the time segment that appears first when going back in time from the start time; and evaluating the appropriateness of the visual confirmation operation to be appropriate when a difference between the start time and the final confirmation time is a threshold value or less.

7. The visual confirmation evaluating apparatus as claimed in claim 1, wherein the storage unit, the position and direction acquiring unit, the viewing information generating unit, and the visual confirmation evaluating unit are provided within a server that is communicable with the vehicle.

8. The visual confirmation evaluating apparatus as claimed in claim 1, wherein the storage unit, the viewing information generating unit, and the visual confirmation evaluating unit are provided within a server that is communicable with the vehicle.

9. The visual confirmation evaluating apparatus as claimed in claim 1, wherein the head position acquiring unit, the line-of-sight acquiring unit, the velocity acquiring unit, the storage unit, the position and direction acquiring unit, the viewing information generating unit, and the visual confirmation evaluating unit are provided within the vehicle.

10. A visual confirmation evaluating method comprising:

acquiring, by a head position acquiring unit, head position data indicating a head position of a driver within a vehicle;

acquiring, by a line-of-sight acquiring unit, line-of-sight data of the driver;

acquiring, by a velocity acquiring unit, velocity data of the vehicle;

storing, by a storage unit, three-dimensional map data representing a map of a real world in which the vehicle travels by three-dimensional shape data, and definition data including an identifier to identify each of intersections, a viewing reference, a confirmation time and an elapsed time;

wherein the definition data define the viewing reference in the three-dimensional map data for each of the intersections identified by the identifier, and the viewing reference is position information of a virtual target that is to be confirmed by the driver when the vehicle enters each of the intersections for each road on right and left directions of each of the intersections;

wherein the confirmation time indicates a time required by the driver to make a visual confirmation that is to be made from a position where each of the intersections is visible, wherein the elapsed time indicates a maximum delay time of a timing at which the driver makes a decision to move the vehicle, acquiring, by a position and direction acquiring unit, position data and direction data indicating a position and a direction of the vehicle in the three-dimensional map data;

generating, by a viewing information generating unit, viewing direction information indicating a direction towards the viewing reference from the head position of the driver indicated by the head position data, and unobstructed state information indicating a state in which the viewing reference is visible from the driver, based on the head position data, the line-of-sight data, the vehicle position data, the direction data, the definition data and the three-dimensional map data; and evaluating, by a visual confirmation evaluating unit, an appropriateness of a visual confirmation operation of the driver, based on the head position data, the line-of-sight data, the vehicle position data, the direction data, the definition data, the unobstructed state information and the viewing direction information.

11. The visual confirmation evaluating method as claimed in claim 10, wherein the acquiring by the position and direction acquiring unit includes generating a road orthographic image that distinguishes a road surface region from other regions, from an image picked up by an on-board camera that is provided in the vehicle and is configured to pick up an image of an outside of the vehicle;

generating an intersection template having a shape of the road surface region, from the three-dimensional map data;

computing a parameter of an image transformation process that matches the road orthographic image and the intersection template; and computing the vehicle position data and the direction data indicating the position and the direction of the vehicle on the three-dimensional map data, respectively, by computing the position and the direction of the vehicle on the road orthographic image and performing an inverse transform based on the parameter.

12. The visual confirmation evaluating method as claimed in claim 10, wherein the generating by the view information generating unit includes computing the head position and the line-of-sight direction of the driver in the three-dimensional map data, based on the position data and the direction data of the vehicle in the three-dimensional map data acquired by the position and direction acquiring unit, the head position data and the line-of-sight data; and generating the unobstructed state information using an intersecting line judging process to judge a line segment that connects the head position of the driver and the viewing reference in the three-dimensional map data and intersects the three-dimensional polygons existing in the three-dimensional map data.

13. The visual confirmation evaluating method as claimed in claim 10, wherein the evaluating by the visual confirmation evaluating unit includes, when the unobstructed state information generated by the viewing information generating unit indicates that the head position is in a range in which the viewing reference is visible from the driver, judging an appropriateness of the line-of-sight direction by comparing the line-of-sight direction of the driver and the viewing direction information in the three-dimensional map data, and judging the line-of-sight direction to be appropriate when a difference between the compared line-of-sight direction and the viewing direction information is within a predetermined range.

14. The visual confirmation evaluating method as claimed in claim 10, wherein the acquiring by the position and direction acquiring unit, the generating by the viewing information generating unit, and the evaluating by the visual confirmation evaluating unit are performed by a server that is communicable with the vehicle.

15. A non-transitory computer-readable storage medium having stored therein a program which, when executed by a computer, causes the computer to perform a process comprising:

first acquiring head position data indicating a head position of a driver within a vehicle;

second acquiring line-of-sight data of the driver;

third acquiring velocity data of the vehicle;

storing, in a storage unit, three-dimensional map data representing a map of a real world in which the vehicle travels by three-dimensional shape data, and definition data including an identifier to identify each of intersections, a viewing reference, a confirmation time and an elapsed time;

wherein the definition data define the viewing reference in the three-dimensional map data for each of the intersections identified by the identifier, and the viewing reference is position information of a virtual target that is to be confirmed by the driver when the vehicle enters each of the intersections for each road on right and left directions of each of the intersections;

wherein the confirmation time indicates a time required by the driver to make a visual confirmation that is to be made from a position where each of the intersections is visible, wherein the elapsed time indicates a maximum delay time of a timing at which the driver makes a decision to move the vehicle, fourth acquiring position data and direction data indicating a position and a direction of the vehicle in the three-dimensional map data;

generating viewing direction information indicating a direction towards the viewing reference from the head position of the driver indicated by the head position data, and unobstructed state information indicating a state in which the viewing reference is visible from the driver, based on the head position data, the line-of-sight data, the vehicle position data, the direction data, the definition data and the three-dimensional map data; and evaluating an appropriateness of a visual confirmation operation of the driver, based on the head position data, the line-of-sight data, the vehicle position data, the direction data, the definition data, the unobstructed state information and the viewing direction information.

16. The non-transitory computer-readable storage medium as claimed in claim 15, wherein the fourth acquiring includes generating a road orthographic image that distinguishes a road surface region from other regions, from an image picked up by an on-board camera that is provided in the vehicle and is configured to pick up an image of an outside of the vehicle;

generating an intersection template having a shape of the road surface region, from the three-dimensional map data;

computing a parameter of an image transformation process that matches the road orthographic image and the intersection template; and computing the vehicle position data and the direction data indicating the position and the direction of the vehicle on the three-dimensional map data, respectively, by computing the position and the direction of the vehicle on the road orthographic image and performing an inverse transform based on the parameter.

17. The non-transitory computer-readable storage medium as claimed in claim 15, wherein the generating includes computing the head position and the line-of-sight direction of the driver in the three-dimensional map data, based on the position data and the direction data of the vehicle in the three-dimensional map data acquired by the fourth acquiring, the head position data and the line-of-sight data; and generating the unobstructed state information using an intersecting line judging process to judge a line segment that connects the head position of the driver and the viewing reference in the three-dimensional map data and intersects the three-dimensional polygons existing in the three-dimensional map data.

18. The non-transitory computer-readable storage medium as claimed in claim 15, wherein the evaluating includes, when the unobstructed state information generated by the generating indicates that the head position is in a range in which the viewing reference is visible from the driver, judging an appropriateness of the line-of-sight direction by comparing the line-of-sight direction of the driver and the viewing direction information in the three-dimensional map data, and judging the line-of-sight direction to be appropriate when a difference between the compared line-of-sight direction and the viewing direction information is within a predetermined range.

19. The non-transitory computer-readable storage medium as claimed in claim 15, wherein the fourth acquiring, the generating, and the evaluating are performed in a server that is communicable with the vehicle.

* * * * *